(12) United States Patent
Obae et al.

(10) Patent No.: US 7,939,101 B2
(45) Date of Patent: May 10, 2011

(54) CELLULOSE POWDER

(75) Inventors: Kazuhiro Obae, Nobeoka (JP); Etsuo Kamada, Nobeoka (JP); Yohsuke Honda, Nobeoka (JP); Shun'ichi Gomi, Nobeoka (JP); Naoaki Yamazaki, Nobeoka (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 621 days.

(21) Appl. No.: 10/332,245

(22) PCT Filed: Jun. 28, 2001

(86) PCT No.: PCT/JP01/05576

§ 371 (c)(1),
(2), (4) Date: Jan. 3, 2003

(87) PCT Pub. No.: WO02/02643

PCT Pub. Date: Jan. 10, 2002

(65) Prior Publication Data

US 2004/0053887 A1    Mar. 18, 2004

(30) Foreign Application Priority Data

Jul. 5, 2000 (JP) ................................ 2000-204000

(51) Int. Cl.
*A61K 9/20* (2006.01)
(52) U.S. Cl. .................................................... 424/465
(58) Field of Classification Search .................. None
See application file for complete search history.

(56) References Cited

U.S. PATENT DOCUMENTS

| | | | | |
|---|---|---|---|---|
| 4,159,345 A | * | 6/1979 | Takeo et al. | 514/781 |
| 5,192,569 A | | 3/1993 | McGinley et al. | |
| 5,574,150 A | * | 11/1996 | Yaginuma et al. | 536/56 |

FOREIGN PATENT DOCUMENTS

| | | |
|---|---|---|
| DE | 2921496 | 2/1980 |
| JP | B-40-26274 | 11/1965 |
| JP | A-50-19917 | 3/1975 |
| JP | A-53-142520 | 12/1978 |
| JP | B-56-2047 | 2/1979 |
| JP | A-61-221115 | 10/1986 |
| JP | A-63-267731 | 11/1988 |
| JP | B-5-38732 | 11/1988 |
| JP | A-1-272643 | 10/1989 |
| JP | A-2-84401 | 3/1990 |
| JP | A-3-36089 | 2/1991 |
| JP | A-5-32542 | 2/1993 |
| JP | A-6-316535 | 11/1994 |
| JP | 08-104650 | * 2/1995 |
| JP | A-8-104650 | 4/1996 |
| JP | 11-152233 | * 11/1997 |
| JP | A-11-152233 | 6/1999 |
| RU | 2050362 | 12/1995 |

* cited by examiner

*Primary Examiner* — Michael G Hartley
*Assistant Examiner* — James W Rogers
(74) *Attorney, Agent, or Firm* — Greenblum & Bernstein, PLC

(57) ABSTRACT

Cellulose powder having an especially excellent balance among moldability, fluidity and disintegrating property is provided. Cellulose powder having an average polymerization degree of 150-450, an average L/D (the ratio of the major axis to the minor axis) value of particles of 75 μm or less of 2.0-4.5, an average particle size of 20-250 μm, an apparent specific volume of 4.0-7.0 cm$^3$/g, an apparent tapping specific volume of 2.4-4.5 cm$^3$/g, and an angle of repose of 55° or less.

15 Claims, No Drawings

CELLULOSE POWDER

TECHNICAL FIELD

The present invention relates to cellulose powder suitable as an excipient for compression molding in medicinal, food and industrial applications. More particularly, the present invention relates to cellulose suitable as an excipient for compression molding that has excellent fluidity and disintegrating properties while retaining good compression moldability, when used in medicinal applications; and to an excipient comprising the cellulose.

BACKGROUND ART

Tabletting of a drug has advantages such as high productivity and easy handling of the resulting tablets during their transportation or upon their use. Therefore, an excipient for compression molding needs to have sufficient moldability to impart such hardness that the tablets are not worn away or destroyed during their transportation or upon their use. Tablets used as medicine are required to be uniform in drug content per tablet in order to accurately exhibit their efficacy. Therefore, when mixed powder of a drug and an excipient for compression molding is compressed into the tablets, a uniform amount of the powder should be packed into the die of a tabletting machine. Accordingly, the excipient for compression molding needs to have not only moldability but also sufficient fluidity. Moreover, the tablets as medicine should have not only the properties described above but also a short disintegration time to rapidly exhibit their efficacy after taking. With an increase of the rate of disintegration, the medicine is dissolved more rapidly in digestive fluid, so that the transfer of the medicine into blood is more rapid, resulting in easy absorption of the medicine. Therefore, the excipient for compression molding should have rapid disintegrating property in addition to moldability and fluidity.

Many active ingredient materials cannot be molded by compression and hence are tabletted by blending with an excipient for compression molding. In general, the larger the amount of the excipient for compression molding blended into the tablets, the higher the hardness of the resulting tablets. The higher the compression stress, the higher the strength of the resulting tablets. Crystalline cellulose is often used as an excipient for compression molding from the viewpoint of safety and the above-mentioned properties.

When an active ingredient and the like which are poor in moldability are tabletted in the field of medicine, an excessive compression stress is unavoidably applied attain a practical tablet hardness. The excessive compression stress on a tabletting machine accelerates the abrasion of dies and punches, and the disintegration time of the resulting tablets is increased. For example, where an amount of an active ingredient, such as a drug, to be blended is large (i.e. where the starting powder has a large specific volume) such as a Chinese orthodox medicine, is blended, or where tablets are miniturized so that the tablets are taken more easily, the problems, such as abrasion or destruction of the tablets during their transportation, are caused since the amount of an excipient blended is so remarkably limited, that desirable tablet hardness cannot be attained. Moreover, there is, for example, the problem that when the active ingredient to be used is that sensitive to striking pressure, such as an enzyme, antibiotic or the like, the active ingredient is inactivated by heat generation by striking pressure or striking pressure per se, it cannot be formulated into tablets because its content is decreased in an attempt to attain a practical hardness. In order to solve such problems, an excipient for compression molding is desired which has sufficient fluidity and disintegrating property and has a moldability higher than before, which can impart a sufficient tablet hardness even when added in a small amount, or impart a sufficient tablet hardness even at a low striking pressure.

For cellulose powder used as an excipient for medicine, compression moldability, disintegrating property and fluidity are desired to be satisfactorily high at the same time. However, since compression moldability and the other properties, i.e., disintegrating property and fluidity are contrary to each other, no previous cellulose powder that has a high moldability has exhibited excellent disintegrating property and fluidity.

Cellulose powder, crystalline cellulose and powdered cellulose have been known and used in medicinal, food and industrial applications.

JP-B-40-26274 discloses crystalline cellulose having an average polymerization degree of 15 to 375, an apparent specific volume of 1.84 to 8.92 cm$^3$/g and a particle size of 300 μm or less. JP-B-56-2047 discloses crystalline cellulose having an average polymerization degree of 60 to 375, an apparent specific volume of 1.6 to 3.1 cm$^3$/g, a specific volume of 1.40 cm$^3$/g or more, a content of powder of 200-mesh size or more of 2-80 wt % and an angle of repose of 35-42°. DE2921496 discloses that cellulose powder having an average polymerization degree of 150 is produced by carrying out acid hydrolysis of a cellulose material in the form of flowable, non-fibrous and water-insoluble cellulose powder to adjust the solid content to 30-40 wt %, followed by drying on trays at 140-150° C. RU2050362 discloses a process in which in order to produce a stable gel of powdered cellulose, powdered cellulose having an average polymerization degree of 400 or less is obtained by impregnating a starting material containing cellulose with a mineral acid or an acid salt solution, and then hydrolyzing the starting material at a high temperature while stirring a starting material layer at a shear rate of 10-1, 000 s$^{-1}$ for 1-10 minutes. The crystalline celluloses and powdered celluloses concretely disclosed in these references, however, are disadvantageous in that the average L/D value of particles of 75 μm or less after drying, the apparent specific volume and the apparent tapping specific volume are so small that the compression moldability is low.

JP-A-63-267731 discloses cellulose powder having a certain average particle size (30 μm or less) and a specific surface area of 1.3 m$^2$/g or more. This cellulose powder involves the following problems because it is produced through a grinding step: its moldability is insufficient because the average L/D value of particles of 75 μm or less is small; its fluidity is low because its particles are small and light; and its disintegrating property is very low because its apparent tapping specific volume is too low.

JP-A-1-272643 discloses cellulose powder having a specified crystal form (cellulose I type), a porosity for pores with a diameter of 0.1 μm or more of 20% or more, and a content of powder of 350-mesh size or more of 90% or more. JP-A-2-84401 discloses cellulose powder having a crystal form of type I, a specific surface area of 20 m$^2$/g or more, a total volume of pores with a diameter of 0.01 μm or more of 0.3 cm$^3$/g or more, and an average particle size of at most 100 μm. Although they have a relatively high moldability, these cellulose powders, however, are different from the cellulose powder of the present invention as the L/D value of dried powder is less than 2.0. In addition, the cellulose powders are not desirable because the nitrogen specific surface area of their particles is too large, so that their conduits are decreased during compression, resulting in low disintegrating property.

Moreover, the cellulose powders disclosed in the above references are obtained by hydrolysis followed by spray drying using an organic solvent as a medium for a slurry before drying. These powders have not been put to practical use because the use of the organic solvent requires, for example, a dryer having an explosion-proof structure and a system for recovering the organic solvent and hence entails high cost.

JP-A-6-316535 discloses crystalline cellulose obtained by acid hydrolysis or alkali oxidative decomposition of a cellulosic material, which has an average polymerization degree of 100-375, an acetic acid retention of 280% or more, compression characteristics represented by Kawakita's equation wherein the constants a and b are 0.85-0.90 and 0.05-0.10, respectively, an apparent specific volume of 4.0-6.0 cm$^3$/g, a specific volume of 2.4 cm$^3$/g or more, a specific surface area of less than 20 m$^2$/g, substantially no particles of 355 μm or more, and an average particle size of 30-120 μm. The crystalline cellulose powder disclosed in the above reference is described as having an excellent balance between moldability and disintegrating property. The angle of repose of the concretely disclosed crystalline cellulose powder of an example having the best balance between moldability and disintegrating property is measured and found to be more than 55°. The fluidity of this crystalline cellulose powder is thus not satisfactory. Particularly when molded under a high striking pressure, the crystalline cellulose disclosed in the above reference can be given a high hardness but has the following problems: the water vapor specific surface area of particles after drying is so small that the conduits in the resulting tablets is decreased to retard the disintegration of the tablets; and in the case of, for example, a recipe in which the proportion of an active ingredient having a low fluidity is high, the coefficient of variation of the weight of the resulting tablets is increased because of the low fluidity to affect the uniformity of the content of a drug.

In addition, JP-A-11-152233 discloses crystalline cellulose having an average polymerization degree of 100-375, a content of particles capable of passing through a 75-μm screen and remaining on a 38-μm screen of 70% or more based on the total weight of the crystalline cellulose, and an average L/D (the ratio of the major axis to the minor axis) value of particles of 2.0 or more. This reference, however, does not describe the angle of repose of the crystalline cellulose disclosed therein. The crystalline cellulose specifically disclosed which is obtained by sieving the crystalline cellulose disclosed in JP-A-6-316535 has problems of worse fluidity and disintegrating property than the crystalline cellulose of JP-A-6-316535 itself. JP-A-50-19917 discloses a process for producing an additive for molding tablets which comprises depolymerizing purified pulp to an average polymerization degree of 450-650 by pretreatment, and subjecting the depolymerization product to mechanical grinding treatment until the apparent tapping specific volume becomes 1.67-2.50 cm$^3$/g and the particle size becomes such a value that 50% or more of the particles pass through a 200-mesh screen. The cellulose powder disclosed in this reference is disadvantageous in that its polymerization degree is so high it exhibits fibrousness, the average L/D value of its particles of 75 μm or less and its apparent specific volume are too large, so that it is poor in disintegrating property and fluidity. The fact that the apparent tapping specific volume of this cellulose powder is small for its apparent specific volume is also a cause for the deterioration of the disintegrating property of tablets obtained by compression.

As described above, no cellulose powder having moldability, fluidity and disintegrating property at the same time with a good balance among them has been known as conventional cellulose powder.

Medicine often has a form of a granular preparation such as granules or fine granules, to which a coating is applied to improve the stability of an active ingredient, adjust the release rate of a drug, mask a taste, or impart enteric properties; or a form of a matrix type granular preparation obtained by granulating a mixture of a coating agent and a drug together with other ingredients. When the granular preparation has a particle size of about 1 mm or less, it is made into capsules in most cases from the viewpoint of ease of handling, but it is preferably made into tablets by compression molding of a mixture of the granular preparation and an excipient, from the viewpoint of cost and ease of taking. However, when granules having a coating film, such as sustained release coated granules, bitter-taste-masked granules, enteric coated granules or the like are tabletted by compression, there is the following problem: the coating film is damaged by compression stress and hence the rate of dissolution and release is increased in mouth, stomach and intestines, so that the exhibition of an expected drug efficacy is not achieved. In order to solve this problem, the following methods have been disclosed. JP-A-53-142520 discloses a method wherein crystalline cellulose is used. JP-A-61-221115 discloses a method wherein crystalline cellulose is used in a proportion of approximately 10-50% based on the amount of tablets. JP-A-3-36089 discloses a method wherein crystalline cellulose having an average particle size of 30 μm or less and a specific surface area of 1.3 m$^2$/g or more is used. JP-A-5-32542 discloses a method wherein crystalline cellulose having a specific surface area of 20 m$^2$/g or more and a porous structure in which the total volume of pores having a diameter of 0.01 μm or more is 0.3 cm$^3$/g or more. JP-A-8-104650 discloses a method wherein a microcrystalline cellulose having an average polymerization degree of 150-220, an apparent specific volume of 4.0-6.0 cm$^3$/g an apparent tapping specific volume of 2.4 cm$^3$/g or more, a specific surface area of less than 20 m$^2$/g, an acetic acid retention of 280% or more, a content of particles of 355 μm or more of less than 5 wt %, a particle size distribution with an average particle size of 30-120 μm, compression characteristics represented by Kawakita's equation wherein the constants a and b are 0.85-0.90 and 0.05-0.10, respectively, and such compression molding characteristics that a cylindrical molded product with a base area of 1 cm$^2$ obtained by compressing 500 mg of the crystalline cellulose at 10 MPa for 10 seconds has a fracture strength in the direction of diameter of 10 kg or more (100 N or more in terms of a fracture strength in SI system of units) and a disintegration time of 100 seconds or less, is used.

The methods disclosed in JP-A-53-142520 and JP-A-61-221115, however, are disadvantageous in that because of the low compression moldability of the microcrystalline cellulose, high compression stress is unavoidably applied in order to attain a practical hardness, so that the damage to the coating film cannot be sufficiently prevented. The method disclosed in JP-A-3-36089 is disadvantageous in that the microcrystalline cellulose has a low fluidity and hence is apt to be separated and segregated from granules during the preparation of tablets. The microcrystalline cellulose disclosed in JP-A-5-32542 is disadvantageous in that it is not practical due to high cost which attributes to the use of an organic solvent for the preparation thereof. In the case where high compression stress cannot be applied, for example, the case where the strength of granules is low, the content of crystalline cellulose should be increased in order to reduce the compression stress.

In such a case, the crystalline cellulose disclosed in JP-A-8-104650 is disadvantageous in that the use of the crystalline cellulose is limited, as it makes the disintegration of the resulting tablets very difficult.

Many active ingredients for medicine are often used after being made into fine particles, and have such a low fluidity that they are not easily compression-molded by a direct compression method (a direct striking method). In particular, the larger the amount of the active ingredient for medicine to be added, the more difficult the compression molding. The above JP-A-8-104650 describes that the use of the above-mentioned microcrystalline cellulose, a fluidizing agent and a disintegrating agent for Chinese orthodox medicine powder or crude drug powder ensures enough fluidity to be subjected to a direct tabletting method, and thus makes it possible to produce tablets having an excellent balance between moldability and disintegrating property. However, in the case where the content of an active ingredient for medicine having a low moldability, which is not limited to Chinese orthodox medicine powder or crude drug powder, is increased in a pharmaceutical composition, there is still a problem that sufficient fluidity cannot be attained. Moreover, if the amount of a disintegrating agent is not sufficient, the retardation of disintegration and a decrease of the rate of dissolution occur. Since an active ingredient powder for medicine is poor in compression moldability and cannot give a molded product without the addition of an excipient, a granule compression method is generally adopted in which compression moldability, disintegrating property and fluidity are assured by carrying out a step of granulating the active ingredient for medicine together with an excipient by a well-known wet or dry process, and then the resulting granules are compression-molded. An extra-granulation method is also often adopted as a means for enhancing the effect of the addition of an excipient by adding the excipient outside the granules besides the excipient added inside the granules upon producing the granules. JP-B-5-38732 discloses a crystalline cellulose having an average particle size of 30 μm or less and a specific surface area of 1.3 m$^2$/g or more. JP-A-8-104650 discloses a process for tabletting, using specific crystalline cellulose, by the granule compression method. These crystalline celluloses, however, are disadvantageous in that when compression stress is increased, the disintegration is retarded and the rate of dissolution is decreased.

DISCLOSURE OF THE INVENTION

The present invention is intended to provide cellulose powder having various properties, i.e., moldability, fluidity and disintegrating property, at the same time with a good balance among them. Furthermore, the present invention is intended to provide the following tablets by incorporating said cellulose powder into the tablets: tablets having high hardness without the retardation of their disintegration, especially when molded under a high striking pressure; granule-containing tablets having less destruction of granules, and less damages to the coating films of the granules and having only a slight change in drug-releasing property when compression molded; and tablets which are uniform in their weight even when their drug content is high, and which have a good balance between hardness and disintegrating property.

In view of the situation described above, the present inventors earnestly investigated and consequently succeeded in controlling the physical properties of cellulose powder to be within specific ranges and found cellulose powder having an excellent balance among various properties, i.e., moldability, fluidity and disintegrating property, whereby the present invention has been accomplished. The present invention is as follows:

(1) cellulose powder having an average polymerization degree of 150-450, an average L/D (the ratio of the major axis to the minor axis) value of particles of 75 μm or less of 2.0-4.5, an average particle size of 20-250 μm, an apparent specific volume of 4.0-7.0 cm$^3$/g, an apparent tapping specific volume of 2.4-4.5 cm$^3$/g, and an angle of repose of 55° or less;

(2) the cellulose powder according to item (1), wherein the average polymerization degree is 230-450;

(3) the cellulose powder according to item (1) or (2), wherein the average polymerization degree is not a level-off polymerization degree;

(4) the cellulose powder according to any one of items (1) to (3), wherein the angle of repose is 54° or less;

(5) the cellulose powder according to any one of items (1) to (4), wherein the cellulose powder has a specific surface area of 85 m$^2$/g or more as measured by water vapor adsorption;

(6) the cellulose powder according to any one of items (1) to (5), wherein a breaking load of tablets obtained by compressing 0.5 g of the cellulose powder at 20 MPa is 170 N or more and the disintegration time of the tablets is 130 seconds or less;

(7) the cellulose powder according to any one of items (1) to (6), wherein the breaking load of tablets obtained by compressing 0.5 g of a mixture of equal amounts of the cellulose powder and lactose at 80 MPa is 150 N or more and the disintegration time of the tablets is 120 seconds or less;

(8) a process for producing cellulose powder, comprising:
i) obtaining a cellulose dispersion containing cellulose particles, wherein
   a) an average polymerization degree is 150-450, and
   b) the average L/D value in wet state is 3.0-5.5,
   by controlling a solution-stirring force in hydrolyzing a natural cellulosic material or in a subsequent step, and
ii) spray-drying the thus obtained cellulose dispersion at an article temperature lower than 100° C.;

(9) the process for producing cellulose powder according to item (8), wherein the average polymerization degree is 230-450;

(10) the process for producing cellulose powder according to item (8) or (9), wherein the average polymerization degree is not a level-off polymerization degree;

(11) the process for producing cellulose powder according to any one of items (8) to (10), wherein the drying step is a step of spray drying at an article temperature lower than 100° C.;

(12) cellulose powder obtained by a production process according to any one of items (8) to (11);

(13) an excipient comprising cellulose powder according to any one of items (1) to (7) and item (12);

(14) a molded product containing cellulose powder according to any one of items (1) to (7) and the item (12) or an excipient according to item (13);

(15) the molded product according to the item (14), wherein the molded product is tablets containing one or more active ingredients;

(16) the molded product according to the item (15), wherein the molded product contains the active ingredient(s) in a proportion of 30 wt % or more;

(17) the molded product according to any one of the items (14) to (16), wherein the molded product contains the active ingredient(s) vulnerable to compression;

(18) the molded product according to the item (17), wherein the active ingredients is coated;

(19) the molded product according to any one of the items (14) to (18), wherein the molded product is rapidly disintegrable; and

(20) the molded product according to any one of the items (14) to (19), wherein the molded product contains a fluidizing agent.

BEST MODE FOR CARRYING OUT THE INVENTION

The present invention is described below in detail.

The cellulose powder according to the present invention should have an average polymerization degree of 150-450, preferably 200-450, more preferably 230-450. When the average polymerization degree is less than 150, the moldability of the cellulose powder is undesirably insufficient. When the average polymerization degree is more than 450, the cellulose powder shows remarkable fibrousness, so that its fluidity and disintegrating property are undesirably deteriorated. When the average polymerization degree is 230-450, the cellulose powder has an especially excellent balance among moldability, disintegrating property and fluidity, and thus preferred. The average polymerization degree is preferably not a level-off polymerization degree. When hydrolysis is carried out to the level-off polymerization degree, the L/D value of particles is liable to be low by a stirring operation in a production process, so that the moldability is undesirably deteriorated. The term "level-off polymerization degree" used herein means a polymerization degree measured by a viscosity method (a copper ethylenediamine method) after hydrolysis carried out under the following conditions: 2.5N hydrochloric acid, boiling temperature, and 15 minutes. It is known that when a cellulosic material is hydrolyzed under mild conditions, its region other than crystals permeable with an acid, i.e., the so-called noncrystalline region is selectively depolymerized, so that the cellulosic material hydrolyzed has a definite average polymerization degree called a level-off polymerization degree (INDUSTRIAL AND ENGINEERING CHEMISTRY, Vol. 42, No. 3, p. 502-507 (1950)). After the polymerization degree reaches the level-off polymerization degree, it does not become lower than the level-off polymerization degree even if the hydrolysis time is prolonged. Therefore, when the polymerization degree is not lowered by hydrolysis of dried cellulose powder under the following conditions: 2.5N hydrochloric acid, boiling temperature, and 15 minutes, it can tell that the polymerization degree has reached the level-off polymerization degree. When the polymerization degree is lowered by the hydrolysis, it can tell that the polymerization degree has not yet reached the level-off polymerization degree.

The polymerization degree should be higher than the level-off polymerization degree by preferably about 5 to about 300, more preferably about 10 to about 250. When the difference is less than 5, it becomes difficult to control the L/D value of particles to be within a specific range, so that the moldability is undesirably deteriorated. When the difference is more than 300, the fibrousness is increased, to give inferior disintegrating property and the fluidity, which is not preferred.

In the cellulose powder according to the present invention, the content of particles capable of remaining on a 250-μm screen is preferably 50 wt % or less. Since particles of more than 250 μm form a dense structure when granulated, their presence in a proportion of more than 50 wt % undesirably deteriorates the moldability and the disintegrating property. The content is preferably 30 wt % or less, more preferably 10 wt % or less, in particular, 5 wt % or less.

The average particle size of the cellulose powder of the present invention should be 20-250 μm. When the average particle size is less than 20 μm, the adhesive and cohesive properties of the cellulose powder are increased, resulting in not only difficult handling but also a low fluidity. When the average particle size is more than 250 μm, the cellulose powder is separated and segregated from an active ingredient, so that the content uniformity of the resulting pharmaceutical composition is undesirably apt to be decreased. The average particle size is preferably 20-120 μm.

In the cellulose powder of the present invention, the average L/D value of particles of 75 μm or less should be 2.0-4.5, preferably 2.2-4.2. When the average L/D value of particles of 75 μm or less is less than 2.0, the plastic deformation properties and the moldability are deteriorated, which is not preferred. When the average L/D value of particles of 75 μm or less is more than 4.5, the fluidity and the disintegrating property are deteriorated, which is not preferred. Moreover, the moldability tends to be deteriorated probably because the cellulose fiber attains fibrousness and tends to have elastic recovery.

Average yield pressure is employed as an indication of the plastic deformation properties of powder. The lower the value of the average yield pressure, the higher the plastic deformation properties and compression moldability of the powder. The highly moldable excipient of the present invention preferably has an average yield pressure of 35 MPa or less when 0.5 g of this powder is compressed to 10 MPa. When the average yield pressure is more than 35 MPa, the moldability is deteriorated, which is not preferred. The average yield pressure is preferably, in particular, 30 MPa or less.

The cellulose powder of the present invention should have an apparent specific volume of 4.0-7.0 $cm^3/g$. When the apparent specific volume is less than 4.0 $cm^3/g$, the moldability is deteriorated. When the apparent specific volume is more than 7.0 $cm^3/g$, the disintegrating property and the fluidity are deteriorated, which is not preferred. Moreover, the moldability tends to be deteriorated probably because the cellulose fiber attains fibrousness and tends to have elastic recovery. The apparent specific volume is preferably 4.0-6.5 $cm^3/g$, in particular, 4.2-6.0 $cm^3/g$.

The apparent tapping specific volume of the cellulose powder of the present invention should be 2.4-4.5 $cm^3/g$, preferably 2.4-4.0 $cm^3/g$, in particular, 2.4-3.5 $cm^3/g$. Even when the apparent specific volume is in a range of 4.0-7.0 $cm^3/g$, if the apparent tapping specific volume is less than 2.4 $cm^3/g$, the disintegrating property of tablets prepared from the cellulose powder are undesirably deteriorated because of excessive consolidation.

The cellulose powder of the present invention should have an angle of repose of 55° or less. When the angle of repose of the cellulose powder is more than 55°, its fluidity is remarkably deteriorated. Particularly when tablets are produced by blending a large amount of an active ingredient with poor fluidity, the weight variation of the tablets becomes remarkable if the fluidity of the excipient for compression molding is low, so that the tablets cannot be put to practical use. The angle of repose of the cellulose powder of the present invention is preferably 54° or less, more preferably 53° or less, in particular, 52° or less. The term "angle of repose" used herein means an angle of repose measured by a powder tester (mfd. by Hosokawa Micron Corporation) after adjusting the water content of the powder to 3.5 to 4.5%. To impart such high fluidity, the cellulose powder preferably has compressibility [%] (=100×(apparent tapping density [$g/cm^3$]−apparent density [g/cm³])/apparent tapping density [g/cm³]) in a specific range. The compressibility is preferably in a range of approximately 30-50%, more preferably 30-49%, in particular, 30-47%.

The terms "apparent tapping density" and "apparent density" used herein mean the reciprocal numbers of the apparent tapping specific volume and apparent specific volume, respectively, defined herein.

The cellulose powder of the present invention preferably has a specific surface area of 85 m²/g or more as measured by water vapor adsorption. When the specific surface area is less than 85 m²/g, an area for water infiltration into particles is small and hence the amount of conduits of the tablets prepared from the cellulose powder is small, to lower disintegrating property of the tablets, which is not preferred. Although the upper limit of the specific surface area is not particularly limited, that of the cellulose powder before drying is about 200 m²/g as a measure because specific surface area is considered as a value which is decreased by drying.

The cellulose powder of the present invention preferably has a specific surface area in a range of 0.5-4.0 m²/g as measured by a nitrogen adsorption method When the specific surface area is less than 0.5 m²/g, the moldability is deteriorated, which is not preferred. When the specific surface area is more than 4.0 m²/g, the disintegrating property are remarkably deteriorated, which is preferred. The specific surface area is preferably 0.8-3.8 m²/g, more preferably 0.8-3.5 m²/g.

When the nitrogen specific surface area is increased, spaces among particles (i.e. conduits) are crushed during compression, so that the disintegrating property tend to be deteriorated. However, even if the nitrogen specific surface area is high, as long as the nitrogen specific surface area is in a definite range, the amount of the conduits can be maintained to prevent the deterioration of the disintegrating property, by controlling the water vapor specific surface area at a definite value or more. A practical physical property value indicating the moldability is the hardness of a molded product. The higher this hardness, the higher the compression moldability. A practical physical property value indicating the disintegrating property is the disintegration time of a molded product. The shorter this disintegration time, the better the disintegrating property. The balance between the tablet hardness and disintegration time of a molded product obtained by compression at a high striking pressure is important in practice, considering that the disintegrating property are generally deteriorated with an increase of the hardness and that the compression at a high striking pressure is unavoidable because many active ingredients for medicine or the like have low moldability.

The breaking load in the direction of diameter of a cylindrical molded product with a diameter of 1.13 cm obtained by compressing 0.5 g of the cellulose powder of the present invention at 20 MPa for 10 seconds is preferably 170 N or more, more preferably 180 N or more, in particular, 190 N or more. The disintegration time (a solution in pure water at 37° C., a disc is present) of the cylindrical molded product is preferably 130 seconds or less, more preferably 120 seconds or less, in particular, 100 seconds or less. The breaking load in the direction of diameter of a cylindrical molded product with a diameter of 1.13 cm obtained by compressing 0.5 g of a mixture of equal amounts of the cellulose powder of the present invention and lactose (Pharmatose 100M, available from DMV Corp.) at 80 MPa for 10 seconds is preferably 150 N or more, more preferably 170 N or more, in particular, 180 N or more. The disintegration time (a solution in pure water at 37° C., a disc is present) of this cylindrical molded product is preferably 120 seconds or less, more preferably 110 seconds or less, in particular, 90 seconds or less.

In addition, a cylindrical molded product with a diameter of 0.8 cm obtained by compressing 0.05 g of the cellulose powder of the present invention at 90 MPa for 10 seconds preferably has adsorption characteristics represented by the following equation (1), after its immersion treatment with acetonitrile solvent:

$$ln[\theta e/(\theta e-\theta)]=Ka \cdot t \quad (1)$$

wherein $Ka \geq 0.0200$ min$^{-1}$, $\theta e$ is the saturated water vapor adsorption rate [%] of tablets at a relative humidity of 55% RH, and $\theta$ is the water vapor adsorption rate [%] of the tablets at a relative humidity of 55% RH and a water vapor adsorption time of t [min.]).

The term "immersion treatment with acetonitrile solvent" used herein means immersing the cylindrical molded product in acetonitrile solvent for 48 hours to permeate the same with the acetonitrile solvent sufficiently, and drying the cylindrical molded product at 25° C. in a nitrogen stream until the relative humidity becomes 0% RH. In the case where the occurrence of moisture absorption or adsorption during operations is conjectured, for example, the case where the linearity of the equation (1) is low, the cellulose surface should be cleaned by vacuum drying with heat. When the Ka value is less than 0.0200 min$^{-1}$, the adsorption rate of water is slow, so that the disintegration time tends to be prolonged, which is not preferred. The effect of the immersion treatment with acetonitrile solvent is conjectured as follows. The compression of the cellulose powder causes an increase of inter-particle hydrogen bonds and crush of micro-spaces (conduits) in particles. When the cylindrical molded product compressed to have a high density is immersed in acetonitrile, acetonitrile enters the micro-spaces (conduits) in particles but not sites of the inter-particle hydrogen bonds to increase the diameter of the conduits.

That is, it can be speculated that with an increase of the number of the inner-particle micro-spaces (conduits) in the cellulose powder which remain in tablets after the compression, the acetonitrile solvent permeates the cellulose powder more easily to increase the diameter of the conduits to give higher water vapor adsorption rate of the tablets. It can also be speculated that since such tablets adsorb water rapidly, their disintegration time in water is reduced. Although the upper limit of the Ka value is not particularly limited, the Ka value is preferably 0.0400 min$^{-1}$ or less because with an increase of the Ka value, the disintegration time tends to be reduced. The Ka value is preferably in a range of 0.0210-0.0400 min$^{-1}$, more preferably 0.0220-0.0400 min$^{-1}$.

A process for producing cellulose powder of the present invention needs to comprise: i) obtaining a cellulose dispersion containing cellulose particles wherein, a) an average polymerization degree is 150-450, and b) the average L/D value in wet state is 3.0-5.5, by controlling a solution-stirring force in hydrolyzing a natural cellulosic material or in a subsequent step, and ii) spray-drying the thus obtained cellulose dispersion at an article temperature lower than 100° C.

The natural cellulosic material referred to herein is a vegetable fibrous material derived from a natural material containing cellulose, such as wood, bamboo, cotton, ramie or the like and is preferably a material having a crystalline structure of cellulose I type. From the viewpoint of production yield, the natural cellulosic material is preferably pulp obtained by purifying such natural materials and preferably has an α-cellulose content of 85% or more.

Conditions for obtaining the cellulose dispersion having an average polymerization degree of 150-450 are, for example, carrying out the hydrolysis under mild conditions in a 0.1-4N aqueous hydrochloric acid solution at 20-60° C. However, when the cellulosic material is hydrolyzed to the level-off polymerization degree, the L/D value of particles is liable to be decreased by stirring operation in the production process, so that the moldability is deteriorated, which is not preferred.

Particles in the cellulose dispersion before drying preferably such that, have the average L/D value of the particles capable of remaining on 75- to 38-μm screens in a range of 3.0-5.5, more preferably 3.2-5.2, when sieved (through JIS standard screens) in a wet state. Since particles in the cellulose dispersion are aggregated by drying, resulting in a small L/D value, cellulose powder having a high moldability and good disintegrating property can be obtained by keeping the average L/D value of particles before drying in a definite range.

The average L/D value of particles before drying can be kept in the definite range by controlling a stirring force in the hydrolyzing reaction or in a subsequent step at a specific intensity.

The stirring during the reaction or in the subsequent step shortens cellulose fiber. When the stirring is too vigorous, the average L/D value of particles is decreased, so that no sufficient moldability can be attained. Therefore, the stirring force should be controlled so that the average L/D value of particles becomes 3.0 or more. When the stirring is too mild, the fibrousness is enhanced, resulting in a low moldability and remarkably deteriorated disintegrating property. Therefore, the stirring force is preferably maintained so that the average L/D value of particles is not more than 5.5.

The intensity of the stirring force can be controlled, for example, in consideration of P/V (kg·m$^{-1}$·sec$^{-3}$) value obtained by the empirical equation (2) described below.

The P/V value, however, is not an absolute numerical value because it is dependent on the size and shape of a agitation vessel, the size and shape of an agitating blade, the number of revolutions, the number of turning blades, etc. The maximum value of P/V in each step before drying ranges from 0.01 to 10,000, and the lower and upper limits of P/V can be determined by controlling the number of revolutions, depending on the kind of the agitation vessel and the agitating blade. It is sufficient that the lower and upper limits is properly determined by comparing values of P/V obtained by varying the agitation vessel used and the number of revolutions of the agitating blade with the average L/D value of particles of 75 μm to 38 μm, for example, as follow, P/V is adjusted so as to fall within a range of 0.3 to 80 in the case where Np=8, V=0.03 and d=0.3; P/V is adjusted so as to fall within a range of 0.01 to 5 in the case where Np=2.2, V=0.07 and d=0.05; and P/V is adjusted so as to fall within a range of 1 to 10,000 in the case where Np=2.2, V=1 and d=1.

$$P/V=(Np \times \rho \times n^3 \times d^5)/V \quad (2)$$

wherein Np (–) is a power number of impeller, ρ (kg/m$^3$) is the density of a liquid, n (rps) is the number of revolutions of the agitating blade, d (m) is the diameter of the agitating blade, and V (m$^3$) is the volume of the liquid.

The cellulose dispersion obtained by the above procedure should be made into powder by drying. The IC (electric conductivity) value of the cellulose dispersion before drying which has been washed and subjected to pH adjustment after the reaction is preferably 200 μS/cm or less. When the IC value is more than 200 μS/cm, the dispersibility of particles in water is deteriorated, resulting in unsatisfactory disintegration. The IC value is preferably 150 μS/cm or less, more preferably 100 μS/cm or less. In preparing the cellulose dispersion, besides water, water containing a low proportion of an organic solvent may be used so long as it does not lessen the effect of the present invention.

For obtaining cellulose powder having a good balance among moldability, fluidity and disintegrating property, spray drying is preferably conducted at an article temperature lower than 100° C. The term "article temperature" used herein means exhaust temperature, not inlet temperature, in the spray drying. In the spray drying, aggregated particles in the cellulose dispersion after the reaction are consolidated by heat shrinkage stress applied from all directions to be densified (become heavy-duty) and attain a good fluidity. Furthermore, the aggregated particles attain good disintegrating property because of weak hydrogen bonds among them. The concentration of the cellulose dispersion before the drying is preferably 25 wt % or less, more preferably 20 wt % or less. When the concentration of the cellulose dispersion is too high, particles are excessively aggregated during the drying and hence the average L/D value of the particles after drying is decreased, so that the bulk density is increased to give a low moldability, which is undesirable. The lower limit of the concentration of the cellulose dispersion is preferably 1 wt % or more. When the lower limit is less than 1 wt %, the fluidity is deteriorated, which is not preferred. Moreover, such a lower limit is not desirable from the viewpoint of productivity because it raises the cost.

As compared with the drying method according to the present invention in which the spray drying is conducted at an article temperature lower than 100° C., the methods as described in JP-A-6-316535 and JP-A-11-152233 wherein a cellulose dispersion is heated at a temperature of 100° C. or higher and then subjected to spray drying or drum drying, or a cellulose dispersion is dried in the form of a thin film without heating, are not preferable because hydrogen bonds among aggregated particles are firmly formed, so that the disintegrating property is deteriorated in these methods. In these methods, cellulose particles in a slurry are easily aggregated in the state where the particles are arranged along the direction of their major axis even if the L/D value of particles before drying is less than the lower limit of a specific range. Therefore, the decrease of the L/D value of particles by drying can be suppressed to give good moldability. However, disintegrating property and fluidity cannot be imparted together with the moldability. Cellulose powder having good fluidity and disintegrating property in addition to good moldability can be obtained only by controlling the L/D value of particles to be within a specific range before drying and conducting spray drying at an article temperature lower than 100° C. For controlling the L/D value of particles before drying to be within a specific range, it is preferred to carry out hydrolysis under conditions where the average polymerization degree does not reach a level-off polymerization degree, as described above.

In addition, for the cellulose powder obtained by drum drying or thin film drying, it is essential to grind it after the drying in order to impart desirable powder physical properties. However, when all particles are ground, the amount of static electricity generated by friction among the particles becomes large probably because the surfaces of the particles become non-dense and uneven. This generation of a large amount of static electricity is not preferable because it also causes deterioration of the fluidity. However, the cellulose powder may be ground after the drying as long as the effect of the present invention is not lessened.

A method in which a slurry before drying is dried after complete or excessive replacement of a solvent in the slurry with an organic solvent is not desirable because capillary force at the time of the evaporation of the organic solvent through spaces among particles is weak as compared with water, so that the formation of interparticle hydrogen bonds is suppressed. Therefore, the nitrogen specific surface area is increased too much to deteriorate the disintegrating property, which is not preferred. The proportion of the organic solvent added is 50 wt % or less, preferably 30 wt % or less, in particular, 20 wt % or less, based on the weight of the solvent in the slurry. Employment of a large amount of the organic solvent is not preferred because it requires large-scale equipments such as an explosion-proof drying equipment and an equipment for recovering the organic solvent and hence entails a high cost.

The loss in weight on drying of the cellulose powder of the present invention is preferably in a range of 8% or less. When the loss in weight on drying is more than 8%, the moldability is deteriorated, which is not preferred.

The excipient referred to herein is that used as a binder, disintegrating agent, granulation assistant, filler, fluidizing agent or the like in the formulation of an active ingredient into a pharmaceutical composition by a well-known method in medicinal, food or industrial applications. The excipient is preferably an excipient for compression molding having an excellent balance among compression moldability, disintegrating property and fluidity.

The molded product referred to herein is a molded product containing the cellulose powder of the present invention and obtained by processing by well-known methods properly selected from mixing, stirring, granulation, compression into tablets, particle size regulation, drying, etc. When used in medicines, the molded product includes, for example, solid pharmaceutical compositions such as tablets, powders, fine granules, granules, extracts, pills, capsules, troches, cataplasmas, etc. The molded product of the present invention includes not only molded products used in medicines but also molded products used in foods (e.g. confectionery, health food, texture improvers, and dietary fiber supplements), solid foundations, bath agents, animal drugs, diagnostic drugs, agrochemicals, fertilizers, ceramics catalysts, etc.

It is sufficient that the molded product referred to herein contains the cellulose powder of the present invention. Although the content of the cellulose powder is not particularly limited, it should be 1 wt % or more based on the weight of the molded product. When the content is less than 1 wt %, satisfactory physical properties cannot be imparted to the molded product; for example, the molded product is worn away or destroyed. The content is preferably 3 wt % or more, more preferably 5 wt % or more.

Furthermore, the molded product referred to herein may freely contain, besides the cellulose powder of the present invention, other additives such as active ingredients, disintegrating agents, binders, fluidizing agents, lubricants, correctives, flavoring materials, coloring matters, sweeteners, surfactants, etc. if necessary.

The disintegrating agents include, for example, celluloses such as sodium croscarmellose, carmellose, calcium carmellose, sodium carmellose, low-substituted hydroxypropyl cellulose, etc.; starches such as sodium carboxymethyl starch, hydroxypropyl starch, rice starch, wheat starch, corn starch, potato starch, partly pregelatinized starch, etc.; and crospovidone.

The binders include, for example, sugars such as white sugar, glucose, lactose, fructose, etc.; sugar alcohols such as mannitol, xylitol, maltitol, erythritol, sorbitol, etc.; water-soluble poly-saccharides such as gelatin, pullulan, carrageenan, locust bean gum, agar, konjak mannan, xanthan gum, tamarind gum, pectin, sodium alginate, gum arabic, etc.; celluloses such as crystalline cellulose, powdered cellulose, hydroxypropyl cellulose, hydroxypropylmethyl cellulose, methyl cellulose, etc.; starches such as pregelatinized starch, starch paste, etc.; synthetic polymers such as poly(vinylpyrrolidone)s, carboxyvinyl polymers, polyvinyl alcohol)s, etc; and inorganic compounds such as calcium hydrogenphosphate, calcium carbonate, synthetic hydrotalcite, magnesium aluminate silicate, etc.

The fluidizing agents include hydrated silicon dioxide, light silicic anhydride, etc. The lubricants include magnesium stearate, calcium stearate, stearic acid, sucrose fatty acid esters, talc, etc. The correctives include glutamic acid, fumaric acid, succinic acid, citric acid, sodium citrate, tartaric acid, malic acid, ascorbic acid, sodium chloride, 1-menthol, etc.

The flavoring materials include orange, vanilla, strawberry, yogurt, menthol, oils (e.g. fennel oil, cinnamon oil, orange-peel oil and peppermint oil), green tea powder, etc. The coloring matters include food colors (e.g. food red No. 3, food yellow No. 5 and food blue No. 1), copper chlorophyllin sodium, titanium oxide, riboflavin, etc. The sweeteners include aspartame, saccharin, dipotassium glycylrrhizinate, stevia, maltose, maltitol, thick malt syrup, powdered sweet hydrangea leaf, etc. The surfactants include phospholipids, glycerin fatty acid esters, polyethylene glycol fatty acid esters, sorbitan fatty acid esters, polyoxyethylenes, hydrogenated castor oil, etc.

The active ingredient referred to herein includes pharmaceutically active ingredients, agrochemical ingredients, ingredients for fertilizer, ingredients for feed, ingredients for food, ingredients for cosmetic, coloring matters, flavoring materials, metals, ceramics, catalysts, surfactants, etc., and may be in any form such as powder, crystals, oil, solution or the like. The active ingredient may be that coated for, for example, the control of dissolution and release or the reduction of a bitter taste.

For example, the pharmaceutically active ingredients are those administered orally, such as antipyretic analgesic antiphlogistics, hypnotic sedatives, sleepiness inhibitors, dinics, infant analgesics, stomachics, antacids, digestives, cardiotonics, drugs for arrhythmia, hypotensive drugs, vasodilators, diuretics, antiulcer drugs, drugs for controlling intestinal function, therapeutic drugs for osteoporosis, antitussive expectorants, antasthmatics, antibacterials drugs for pollakiurea, tonics, vitamin preparations, etc.

The content of the active ingredient(s) in the molded product of the present invention is 0.01 to 99 wt % based on the weight of the molded product. When the content of the active ingredient(s) is less than 0.01 wt %, no sufficient drug efficacy can be expected. When the content is more than 99 wt %, the content of the excipient is not sufficient, so that satisfactory physical properties cannot be imparted; for example, the molded product is worn away or destroyed.

When the cellulose powder of the present invention is used in the case where the content of the active ingredient(s) in the molded product is high, it is especially advantageous because it has, for example, the following advantages: it can impart a sufficient moldability without accelerating the retardation of disintegration even at a high striking pressure; it permits reduction of the amount of the cellulose powder to be added and hence miniaturization of the molded product; and the degree of wear of the resulting tablets is low and their powdering and breakage during packing into bottles and transportation is minimal. The cellulose powder of the present invention is advantageous when the content of the active ingredient(s) is 5 wt % or more, preferably 10 wt % or more, still more preferably 30 wt % or more, in particular, 50 wt % or more.

Since the cellulose powder of the present invention has an excellent compression moldability, it can be molded with a small blending amount thereof or a low compressive force and hence is very suitable for tabletting the active ingredient(s). The cellulose powder of the present invention enables the tabletting of a pharmaceutically active ingredient with poor moldability, the miniaturization of large tablets of a Chinese orthodox medicine, crude drug, cold remedy, vitamin preparation or the like, and the preparation of intraoral rapidly soluble tablets, granule-containing tablets, or the like.

The tablets referred to herein are molded products containing the cellulose powder of the present invention and optionally other additives and obtained by any of a direct tabletting method, a granule compression method and an extra-granulation method. Tablets obtained by direct compression are especially preferable.

The cellulose powder of the present invention is especially advantageously used for an active ingredient for medicine having a low moldability, because of the advantages, for example, that compression into tablets can be carried out at a high striking pressure without accelerating the retardation of disintegration. Whether the moldability is low or not can be determined by the hardness of tablets obtained by placing 0.5 g of the pharmaceutically active ingredient in a die (manufactured by Kikusui Seisakusho Ltd. from material SUK 2,3) and compressing the active ingredient with a flat punch and a base area of 1 cm$^2$ (manufactured by Kikusui Seisakusho Ltd. from material SUK 2,3) until the pressure becomes 100 MPa (a static compressing machine such as PCM-1A manufactured by Aikoh Engineering Co., Ltd. is used and the compression rate is approximately 20-30 cm/min). The cellulose powder of the present invention is especially effectively used when the tablet hardness of the pharmaceutically active ingredient is less than 100 N, preferably less than 50 N, more preferably less than 10 N. Such a drug includes phenacetin, acetaminophen, ethenzamide, etc.

When the cellulose powder of the present invention is used in combination with a fluidizing agent and a disintegrating agent, tablets especially excellent in moldability and disintegrating property can be produced without deteriorating the fluidity during the production of the tablets. As the disintegrating agent, a super-disintegrating agent such as sodium croscarmellose (e.g. "Ac-Di-Sol" manufactured by FMC Corp.) is preferably used because it is effective even when added in a small amount. As the fluidizing agent, light silicic anhydride is especially preferable, and the fluidizing agent includes "Aerosil" (mfd. by Nippon Aerosil Co., Ltd.), "Carplex" (mfd. by Shionogi & Co., Ltd.), "Cyroid" (mfd. by Fuji Davisson Co., Ltd.), "Adsolider" (mfd. by Freund Sangyo K. K.), etc. Although the proportions of the components described above are not particularly limited, suitable examples thereof are as follows: the microcrystalline cellulose of the present invention 1 to 99 wt %, the disintegrating agent 0.5 to 20 wt %, and the fluidizing agent 0.1 to 5 wt %.

It is preferable to adopt a method comprising premixing the active ingredient(s) and the fluidizing agent at first, mixing therewith the cellulose powder of the present invention, the disintegrating agent and optionally other additives, and then making the resulting mixture into tablets, because this method gives higher fluidity and moldability than a method in which all the components are mixed at once. With a decrease of the fluidity of the active ingredient(s) and an increase of the proportion of the active ingredient(s), the timing of addition of the fluidizing agent has a more remarkable effect.

Particularly when rapidly-disintegrating property is required, the molded product of the present invention is especially effective since the molded product of the present invention can have a sufficient hardness even when produced at a low striking pressure and thus may be made thick, so that many conduits can be left in the molded product. The term "rapidly-disintegrating property" means that a molded product is disintegrated within 1 minute in a medium such as water, artificial gastric juice, artificial intestinal juice, saliva or the like. Pharmaceutical compositions having such a characteristic include intraoral rapidly-soluble tablets, intraoral rapidly-disintegrable tablets, etc.

The cellulose powder of the present invention is very suitable also for tabletting, for example, granules each having a coating film. When a mixture of coated granules, the cellulose powder of the present invention and optionally other additives are made into tablets, a practical hardness can be attained even if the compression stress is greatly reduced. Therefore, damages to the coating films by the compression stress can be suppressed, so that the mixture can be made into tablets while enabling the granules to retain their expected dissolving and releasing properties.

The active ingredient vulnerable to compression herein is, for example, an active ingredient which is inactivated by compression stress or heat, or an active ingredient which cannot exhibit expected dissolving and releasing properties because the coating portion of the active ingredient is damaged by pressure.

The molded product containing a coated active ingredient(s) of the present invention refers to a molded product having the molded product form defined above, such as powder, granular preparations (e.g. fine granules or granules), or the like and containing one or more active ingredients, wherein the active ingredient(s) per se is coated with a film; particles made of the active ingredient(s) and additives are coated with a film; the active ingredient(s) is coated by granulating a mixture of the active ingredient(s) and a coating agent; or the mixture thereof. The coating agent is used, for example, masking a taste, imparting sustained-release properties or enteric properties, or preventing moisture, and includes, for example, cellulose type coating agents (e.g. ethyl cellulose, hydroxypropylmethyl cellulose phthalate, carboxymethylethyl cellulose, hydroxypropylmethyl cellulose acetate succinate, cellulose acetate succinate, cellulose acetate phthalate, and cellulose acetate), acrylic polymer type coating agents (e.g. Eudragit RS, Eudragit L and Eudragit NE), shellac and silicone resins. These may be used singly or in combination. As a method for using these coating agents, a well-known method may be used. The coating agent may be dissolved in an organic solvent or suspended in water. The coating agent suspended in water may be freely granulated together with one or more active ingredients for medicine and other components.

With an increase of the proportion of the cellulose powder of the present invention blended in the molded product containing one or more coated active ingredients of the present invention, the suppression of the damage to the coating film by the cellulose powder becomes more effective. The proportion to be blended is preferably 1 to 90 wt %. When the proportion is less than 1 wt %, no sufficient effect can be obtained. When the proportion is more than 90 wt %, the proportion of the active ingredient(s) is undesirably insufficient. The proportion is more preferably 5 to 80 wt %, in particular, 5 to 70 wt %.

The cellulose powder of the present invention can be used in wet granulation as, for example, a reinforcing agent for a sugar coating in sugar-coated tablets, an extrudability improver in extrusion granulation, or a granulation assistant in crushing granulation, fluidized-bed granulation, high-shear granulation, tumbling fluidized-bed granulation or the like, and permits preparation of a granular pharmaceutical composition or granules to be compressed into tablets. For preparing the granules to be compressed into tablets, a dry granulation method may be adopted. In addition, tabletting by the method wherein the cellulose powder of the present invention is added to such granules that are obtained by a well-known method and the mixture is compression molded (an extra-granulation method) is also applicable. Since the cellulose powder of the present invention has high water absorption properties, the rate of granulation can be reduced even when a highly water-soluble pharmaceutical active ingredient is granulated. It, therefore, reduces the formation of coarse particles and, thus, contributes to the increase of granulation yield. The cellulose powder of the present invention gives a bulky granulation product because of its low particle density and hence contributes also to the preparation of granules for compression tabletting with high compression moldability. Furthermore, the cellulose powder of the present invention may be blended into a powder in order to, for example, prevent blocking or improve the fluidity, or it may be blended into capsules in order to, for example, improve the degree of filling.

The present invention is described in detail by way of the following examples, which do not limit the scope of the invention. Method for measuring physical properties in the examples and comparative examples are as follows.

1) Average Polymerization Degree

A value measured by the copper ethylenediamine solution viscosity method described in the crystalline cellulose identification test (3) in the 13th revised Japanese Pharmacopoeia.

2) L/D of Particles before Drying

The average L/D value of particles in a cellulose dispersion before drying was measured as follows. The cellulose dispersion was sifted through JIS standard screens (Z8801-1987), and a photo-micrograph of particles that had passed through a 75-μm screen and had remained on a 38-μm screen was subjected to image analysis processing (apparatus: Hyper 700, software: Imagehyper, manufactured by Interquest Inc.). L/D of the particles was defined as the ratio between the long side and short side (long side/short side) of a rectangle having the smallest area among rectangles circumscribed about any of the particles. As the average L/D value of the particles, the average of the L/D values of at least 100 of the particles was used.

3) Loss in Weight on Drying [%].

After 1 g of powder was dried at 105° C. for 3 hours, the loss in weight was expressed as a percentage by weight.

4) Proportion of Particles Capable of Remaining on a 250-μm Screen [%]

Using a low-tap type sieve shaker (Sieve Shaker Model A, mfd. by Heikoh Seisaku-sho Co., Ltd.), 10 g of a sample was sifted through a JIS standard screen (Z8801-1987) with a screen opening of 250 μm for 10 minutes, and the weight of particles remaining on the 250-μm screen was expressed as a percentage by weight based on the total weight.

5) Average L/D Value of Particles of 75 μm or Less

A photomicrograph of particles that had passed through a 75-μm JIS standard screen in sifting with Air Jet Sieve (Model A200LS, mfd. by ALPINE) was subjected to image analysis processing (apparatus: Hyper 700, software: Imagehyper, manufactured by Interquest Inc.). L/D was defined as the ratio between the long side and short side (long side/short side) of a rectangle having the smallest area among rectangles circumscribed about any of the particles. As the average L/D value of the particles, the average of the L/D values of at least 400 of the particles was used.

The average L/D value should be measured after previously making the particles discrete so that they are not entangled with one another.

6) Apparent Specific Volume [cm³/g]

A powder sample was roughly packed into a 100-cm³ glass measuring cylinder over a period of 2-3 minutes by the use of a metering feeder or the like, and the top surface of the powder layer was made level with a soft brush such as a writing brush, after which the volume of the powder sample was read. The apparent specific volume was expressed as a value obtained by dividing the read value by the weight of the powder sample. The weight of the powder was properly determined so that its volume might be approximately 70-100 cm³.

7) Apparent Tapping Specific Volume [cm³/g]

Using a commercial powder physical property measuring machine (Powder Tester Model T-R, mfd. by Hosokawa Micron Corporation), a 100-cm³ cup was filled with powder and tapped 180 times. Then, the apparent tapping specific volume was calculated by dividing the volume of the cup by the weight of the powder layer remaining in the cup.

8) Angle of Repose [°]

The water content of powder (measured by means of an infrared moisture meter (Model FD-220, mfd. by KETT Science Laboratory; 1 g. 105° C.)) was adjusted to 3.5-4.5%. Thereafter, using a commercial powder physical property measuring machine (Powder Tester Model T-R, mfd. by Hosokawa Micron Corporation), the powder fell under the following conditions: a metal funnel (made of a material incapable of generating static electricity) with an orifice diameter of 0.8 cm, and vibration graduation 1.5. The angles of the ridgelines (the angles of two ridgelines; measurement distance 3°) of a heap formed by the powder were measured. The angle of repose [°] was expressed as the average of three measurements.

9) Compressibility [%]

Compressibility was calculated by the following equation (3) by using the apparent specific volume and apparent tapping specific volume defined above:

$$\text{Compressibility} = 100 \times [(1/\text{apparent tapping specific volume}) - (1/\text{apparent specific volume})]/(1/\text{apparent tapping specific volume}) \quad (3)$$

10) Average Particle Size [μm]

Using a low-tap type sieve shaker (Sieve Shaker Model A, mfd. by Taira Kosaku-sho Co., Ltd.) and JIS standard screens (Z8801-1987), 10 g of a powder sample was sieved for 10 minutes to measure the particle size distribution. The average particle size was expressed as a particle size corresponding to a cumulative weight percentage of 50%.

11) Water Vapor Specific Surface Area [m²/g]

Using a dynamic water vapor adsorption apparatus DVS-1 (mfd. by Surface Measurement Systems Ltd.) and water vapor as an adsorption gas, the amount of water vapor adsorbed by a sample was measured in a range of 0-30% RH according to the measuring steps described below, and the water vapor specific surface area was calculated by a BET method. The calculation was carried out by taking the molecular occupied area of water as 8.1 Å. As the sample, 0.01-0.02 g of a sample obtained by removing water from about 0.10 g of cellulose powder by vacuum drying in 5-cm³ sample tube at 100° C. for 3 hours was placed in the aforesaid apparatus and subjected to the measurement.

(Measuring Steps)

The sample was allowed to stand at each of the following relative humidities for the following measurement time and the amount of water vapor adsorbed onto the sample was measured.

| Relative humidity | Measurement time |
|---|---|
| 0% RH | 200 min. or less |
| 3% RH | 150 min. or less |
| 6, 9, 12, 15, 18, 21, 24, 27 or 30% RH | 100 min. or less. |

12) Nitrogen Adsorption Specific Surface Area [m²/g]

Measured by a BET method using a Flowsorb II2300 manufactured by Shimadzu Corp. and nitrogen as an adsorption gas.

13) Average Yield Pressure [MPa]

The water content (measured by means of an infrared moisture meter (Model FD-220, mfd. by KETT Science Laboratory; 1 g, 105° C.)) of powder was adjusted to 3.5-4.5%. Then, 0.5 g of a sample of the powder was placed in a die (manufactured by Kikusui Seisakusho Ltd. from material SUK 2,3) and compressed with a flat punch having a base area of 1 cm² (manufactured by Kikusui Seisakusho Ltd. from material SUK 2,3) until the pressure became 10 MPa (a compressing machine PCM-1A manufactured by Aikoh Engineering Co., Ltd. was used and the compression rate was adjusted to 1 cm/min). A stress P and the height h [cm] of the powder layer at the stress P were input into a computer at a data input rate of 0.02 second and recorded therein.

The relationship between the stress P and ln[1/(1−D)] calculated from the volume V [cm³] of the powder layer at the stress P was graphically illustrated, followed by linear regression in a stress P [MPa] range of 2-10 MPa by a method of least squares. The average yield pressure was defined as the reciprocal number of the slope k of the regression line. V [cm³] was expressed as the product of the base area (1 cm²) of the punch with a flat surface and the height h [cm] of the powder layer at the stress P. The height h of the powder layer should be measured without strain in the system of the compressing machine (the total strain in the die, punch, load cell, plunger, etc.). D was calculated by the following equation (4):

$$D=[(0.5\times(1-W/100))/V]/1.59 \quad (4)$$

wherein D is the packing rate of tablets, W is the water content [%] measured by means of an infrared moisture meter (Model FD-220, mfd. by KETT Science Laboratory; 1 g, 105° C.), and the value 1.59 is the true density [g/cm³] of the cellulose powder measured with an air comparison type gravimeter (Pycnometer 930, mfd. by Beckmann AG).

14) Water Vapor Adsorption Rate of Tablets Ka [1/min]

A cylindrical molded product with a diameter of 0.8 cm obtained by compressing 0.05 g of a sample at 90 MPa for 10 seconds (a compressing machine PCM-LA manufactured by Aikoh Engineering Co., Ltd. was used and the compression rate was adjusted to 29 cm/min) was immersed in acetonitrile (for liquid chromatography) for 48 hours, placed in a dynamic vapor adsorption measurement apparatus (Model DVS-1, mfd. by Microtec Nichion Co., Ltd.), and then dried at 25° C. and a relative humidity of 0% RH in a nitrogen stream until the tablet weight reached sufficient equilibrium (the degree of variability of the weight for 5 minutes was 0.0015%/min or less). Then, the relative humidity was set at 55% RH, and the tablet weight was recorded every 1 minute until the tablet weight reached equilibrium (the degree of variability of the weight for 5 minutes was 0.0015%/min or less). The relationship between the water vapor adsorption time t and ln[θe/(θe−θ)] was graphically illustrated, followed by linear regression in a range of 20-100 minutes by a method of least squares. The slope of the regression line was taken as Ka. The saturated water vapor adsorption rate θe[%] of the tablet at a relative humidity of 55% RH and the water vapor adsorption rate θ[%] of the tablet at a relative humidity of 55% RH and a water vapor adsorption time of t were calculated as follows:

$$\theta e=100\times ms/m_0[\%] \quad (5)$$

$$\theta=100\times mt/m_0[\%] \quad (6)$$

wherein $m_0$ is a tablet weight [g] at the time when equilibrium was sufficiently reached at a relative humidity of 0% RH, mt is a tablet weight [g] at a relative humidity of 55% RH and a water vapor adsorption time of t, and ms is a tablet weight [g] at the time when equilibrium was sufficiently reached at a relative humidity of 55% RH.

15) Hardness [N]

Using a Schleuniger hardness meter (Model 6D, mfd. by Freund Sangyo K. K.), a load was applied to a cylindrical molded product or a tablet in the direction of diameter, and a load at the time of the destruction thereof was measured. The hardness was expressed as the number average of load values obtained for five samples. A cylindrical molded product of 100% cellulose powder and a cylindrical molded product of a mixture of equal amounts of cellulose powder and lactose were produced as follows. In a die (manufactured by Kikusui Seisakusho Ltd. from material SUK 2,3) was placed 0.5 g of a sample, and compressed with a flat punch having a diameter of 1.13 cm (base area: 1 cm²) (manufactured by Kikusui Seisakusho Ltd. from material SUK 2,3). The cylindrical molded product of 100% cellulose powder was produced by compression at 20 MPa and maintenance of the compression stress for 10 seconds (a compressing machine PCM-1A manufactured by Aikoh Engineering Co., Ltd. was used and the compression rate was adjusted to about 10 cm/min). The cylindrical molded product of a mixture of equal amounts of cellulose powder and lactose was produced by compression at 80 MPa and maintenance of the compression stress for 10 seconds (a compressing machine PCM-1A manufactured by Aikoh Engineering Co., Ltd. was used and the compression rate was adjusted to about 25 cm/min).

16) Disintegration Time [Seconds]

A disintegration test was carried out according to the general test method and tablet disintegration test method prescribed in the 13th revised Japanese Pharmacopoeia. The disintegration time of cylindrical molded articles or tablets in pure water at 37° C. was measured by means of a disintegration tester (Model NT-40HS, mfd. by Toyama Sangyo Co., Ltd., fitted with a disc). The disintegration time was expressed as the number average of values measured for six samples.

17) CV Value of Tablets [%]

Ten tablets were accurately weighed and the CV value was defined as the coefficient of variation of the tablet weight.

18) Degree of Wear of Tablets [%]

The weight (Wa) of 20 tablets was measured, and the tablets were placed in a tablet degree-of-wear tester (mfd. by PTFR-A, PHARMA TEST), followed by revolution at 25 rpm for 4 minutes. Then, fine powder adhering to the tablets was removed and the weight (Wb) of the tablets was measured again. The degree of wear was calculated by the equation (7):

$$\text{Degree of wear}=100\times(Wa-Wb)/Wa \quad (7)$$

19) Rate of Dissolution of a Drug [%]

The rate of dissolution is measured by a paddle method by using an automatic dissolution tester DT-610 (mfd. by Nippon Bunko Kogyo Co., Ltd.). As a test liquid, the first liquid among the test liquids in the general, test method and degradation test method prescribed in the 13th revised Japanese Pharmacopoeia. The measurement was carried out three times and the average of the measured values was calculated.

Example 1

Two kilograms of commercially available SP pulp (polymerization degree: 1030, and level-off polymerization degree: 220) was chopped, placed in 30 L of a 4N aqueous hydrochloric acid solution, and then hydrolyzed at 60° C. for 72 hours with stirring (rate of stirring: 10 rpm) by a low-rate stirrer (30LGL reactor, mfd. by Ikebukuro Hohroh Kogyo Co., Ltd.; blade diameter: about 30 cm). The resulting acid-insoluble residue was filtered by the use of a Buchner funnel, and the filtration residue was washed 4 times with 70 L of pure water, neutralized with aqueous ammonia, and then placed in a 90-L polyethylene bucket. Pure water was added thereto and the resulting mixture was made into a cellulose dispersion having a concentration of 10% (pH: 6.7, and IC: 45 µS/cm), while being stirred (rate of stirring: 100 rpm) with Three-One Motor (Type 1200G, 8M/M, mfd. by HEIDON; blade diameter: about 5 cm).

The cellulose dispersion was subjected to spray drying (dispersion feed rate 6 L/hr, inlet temperature 180 to 220° C., and outlet temperature 50 to 70° C.) to obtain cellulose powder A (loss in weight on drying: 3.5%). Table 1 shows physical properties of cellulose powder A and physical properties of a cylindrical molded product obtained by compressing 100% cellulose powder A. Table 2 shows physical properties of a cylindrical molded product obtained by compressing a mixture of equal amounts of cellulose powder A and lactose.

Example 2

Cellulose powder B (loss in weight on drying: 4.2%) was obtained by the same procedure as in Example 1 except for using commercially available SP pulp (polymerization degree: 790, and level-off polymerization degree: 220) and changing the hydrolysis conditions to: 4N, 40° C. and 48 hours, the concentration of the cellulose dispersion to 8%, its pH to 6.0, and its IC to 35 µS/cm. Table 1 shows physical properties of cellulose powder B obtained and physical properties of a cylindrical molded product obtained by compressing 100% cellulose powder B. Table 2 shows physical properties of a cylindrical molded product obtained by compressing a mixture of equal amounts of cellulose powder B and lactose.

Example 3

Cellulose powder C (loss in weight on drying: 3.8%) was obtained by the same procedure as in Example 2 except for changing the rate of stirring during the reaction to 5 rpm, the concentration of the cellulose dispersion to 12% (rate of stirring for preparing the dispersion: 50 rpm), its pH to 6.5, and its IC to 40 µS/cm. Table 1 shows physical properties of cellulose powder C obtained and physical properties of a cylindrical molded product obtained by compressing 100% cellulose powder C. Table 2 shows physical properties of a cylindrical molded product obtained by compressing a mixture of equal amounts of cellulose powder C and lactose.

Example 4

Cellulose powder D (loss in weight on drying: 3.2%) was obtained by the same procedure as in Example 2 except for changing the concentration of the cellulose dispersion to 16%, its pH to 6.9, and its IC to 65 µS/cm. Table 1 shows physical properties of cellulose powder D obtained and physical properties of a cylindrical molded product obtained by compressing 100% cellulose powder D. Table 2 shows physical properties of a cylindrical molded product obtained by compressing a mixture of equal amounts of cellulose powder D and lactose.

Example 5

Cellulose powder E (loss in weight on drying: 4.0%) was obtained by the same procedure as in Example 2 except for changing the hydrolysis conditions to a 3N aqueous hydrochloric acid solution, 40° C. and 40 hours, the concentration of the cellulose dispersion to 8%, its pH to 6.3, and its IC to 38 µS/cm. Table 1 shows physical properties of cellulose powder E obtained and physical properties of a cylindrical molded product obtained by compressing 100% cellulose powder E. Table 2 shows physical properties of a cylindrical molded product obtained by compressing a mixture of equal amounts of cellulose powder E and lactose.

Example 6

Cellulose powder F was obtained by the same procedure as in Example 1 except for using commercial SP pulp (polymerization degree: 870, and level-off polymerization degree: 2203, and changing the hydrolysis conditions to a 3N aqueous hydrochloric acid solution, 40° C. and 24 hours, the rate of stirring during the reaction to 15 rpm, the concentration of the cellulose dispersion to 8%, its pH to 5.7, and its IC to 30 µS/cm. Table 1 shows physical properties of cellulose powder F obtained and physical properties of a cylindrical molded product obtained by compressing 100% cellulose powder F. Table 2 shows physical properties of a cylindrical molded product obtained by compressing a mixture of equal amounts of cellulose powder F and lactose.

Example 7

Cellulose powder G was obtained by the same procedure as in Example 1 except for changing the hydrolysis conditions to a 3N aqueous hydrochloric acid solution, 40° C. and 20 hours, the rate of stirring during the reaction to 20 rpm, the concentration of the cellulose dispersion to 6%, its pH to 7.1, and its IC to 180 µS/cm. Table 1 shows physical properties of cellulose powder G obtained and physical properties of a cylindrical molded product obtained by compressing 100% cellulose powder G Table 2 shows physical properties of a cylindrical molded product obtained by compressing a mixture of equal amounts of cellulose powder G and lactose.

Comparative Example 1

Commercial SP pulp (polymerization degree: 790, and level-off polymerization degree: 220) was hydrolyzed in 30 L of a 3N aqueous hydrochloric acid solution at 105° C. for 30 minutes with stirring (rate of stirring: 30 rpm) by a low-rate stirrer (30LGL reactor, mfd. by Ikebukuro Hohroh Kogyo Co., Ltd.; blade diameter: about 30 cm). The resulting acid-insoluble residue was filtered by the use of a Buchner funnel, and the filtration residue was washed 4 times with 70 L of pure water, neutralized with aqueous ammonia, and then placed in a 90-L polyethylene bucket. Pure water was added thereto and the resulting mixture was made into a cellulose dispersion having a concentration of 17% (pH: 6.4, and IC: 12 µS/cm), while being stirred (rate of stirring: 500 rpm) with a Three-One Motor (Type 1200G, 8M/M, mfd. by HEIDON; blade diameter: about 5 cm).

The cellulose dispersion was dried in a drum dryer (Model KDD-1 of Kusunoki Seisakusho Co., Ltd., steam pressure:

0.35 MPa, drum surface temperature: 136° C., number of revolutions of drum: 2 rpm, and temperature of the dispersion in a reservoir: 100° C.) and then ground with a hammer mill, and coarse particles were re moved by a screen with opening of 425 μm to obtain cellulose powder H (loss in weight on drying: 3.9%, corresponding to Example 1 described in JP-A-6-316535). Table 1 shows physical properties of cellulose powder H obtained and physical properties of a cylindrical molded product obtained by compressing cellulose powder H. Table 2 shows physical properties of a cylindrical molded product obtained by compressing a mixture of equal amounts of cellulose powder H and lactose.

Comparative Example 2

Two kilograms of commercial SP pulp (polymerization degree: 1030, and level-off polymerization degree: 220) was chopped and then hydrolyzed in 30 L of a 0.14N aqueous hydrochloric acid solution at 121° C. for 1 hour with stirring (rate of stirring: 30 rpm) by a low-rate stirrer (30LGL reactor, mfd. by Ikebukuro Hohroh Kogyo Co., Ltd.; blade diameter: about 30 cm). The resulting acid-insoluble residue was filtered by the use of a Buchner funnel, and the filtration residue was washed 4 times with 70 L of pure water, neutralized with aqueous ammonia, placed in a 90-L polyethylene bucket, and then made into a cellulose dispersion having a concentration of 17% (pH: 6.4, and IC: 64 μS/cm), while being stirred (rate of stirring: 500 rpm) with a Three-One Motor (Type 1200G, 8M/M, mfd. by HEIDON; blade diameter: about 5 cm).

The cellulose dispersion was subjected to spray drying (dispersion feed rate: 6 L/hr, inlet temperature: 180 to 220° C., and outlet temperature: 70° C.), after which coarse particles were removed by a 325-mesh screen to obtain cellulose powder I (loss in weight on drying: 4.1%, corresponding to Example 1 in JP-B-40-26274). Table 1 shows physical properties of cellulose powder I obtained and physical properties of a cylindrical molded product obtained by compressing cellulose powder I. Table 2 shows physical properties of a cylindrical molded product obtained by compressing a mixture of equal amounts of cellulose powder I and lactose.

Comparative Example 3

A pulp sheet of needle leaf tree and broad-leaf tree for dissolution (α-cellulose 90.5%, β-cellulose 4.7%, cuprammonium relative viscosity 4.70, and whiteness 93) was disintegrated, immersed in 12 L of a sodium hypochlorite solution (available chloride: 1.6 g/L) to adjust the pH to 10.9, and then treated at 60° C. for 310 minutes. The pulp thus treated was thoroughly washed with water, centrifugally dehydrated, and then dried by air blowing at 105° C. The pulp dried was ground with an oscillating ball mill for 30 minutes, after which coarse particles were removed with a 100-mesh screen to obtain cellulose powder J (loss in weight on drying: 2.0, corresponding to Example 2 in JP-A-50-19917). Table 1 shows physical properties of cellulose powder J obtained and physical properties of a cylindrical molded product obtained by compressing cellulose powder J. Table 2 shows physical properties of a cylindrical molded product obtained by compressing a mixture of equal amounts of cellulose powder J and lactose.

Comparative Example 4

Commercial KP pulp (polymerization degree: 840, and level-off polymerization degree: 145) was hydrolyzed in a 0.7% aqueous hydrochloric acid solution at 125° C. for 150 minutes, and the hydrolysis residue was neutralized, washed and then filtered to obtain a wet cake. The wet cake was thoroughly ground in a kneader, after which ethanol was added thereto so that the volume ratio of ethanol to the ground product of the cake becomes 1. The resulting mixture was filtered by expression and then air-dried. The resulting dried powder was ground with a hammer mill and coarse particles were removed with a 40-mesh screen to obtain cellulose powder K (loss in weight on drying: 3.0%, corresponding to Example 1 in JP-A-56-2047). Table 1 shows physical properties of cellulose powder K obtained and physical properties of a cylindrical molded product obtained by compressing cellulose powder K. Table 2 shows physical properties of a cylindrical molded product obtained by compressing a mixture of equal amounts of cellulose powder K and lactose.

Comparative Example 5

Cellulose powder I of Comparative Example 2 was ground with a pneumatic grinding mill (Single-Track Jet Mill Model STJ-200, mfd. by Seishin Enterprise Co., Ltd.), and coarse particles were removed by a screen with a opening of 75 μm to obtain cellulose powder L (loss in weight on drying: 4.1%, corresponding to Example 1 in JP-A-63-267731). Table 1 shows physical properties of cellulose powder L obtained and physical properties of a cylindrical molded product obtained by compressing cellulose powder L. Table 2 shows physical properties of a cylindrical molded product obtained by compressing a mixture of equal amounts of cellulose powder L and lactose.

Comparative Example 6

Cellulose powder E of Example 5 was ground with a magnetic ball mill for 12 hours to obtain cellulose powder M (loss in weight on drying: 5.1%). Table 1 shows physical properties of cellulose powder M obtained and physical properties of a cylindrical molded product obtained by compressing cellulose powder M. Table 2 shows physical properties of a cylindrical molded product obtained by compressing a mixture of equal amounts of cellulose powder M and lactose.

Comparative Example 7

The same process as in Comparative Example 2 was carried out except for changing the hydrolysis conditions to a 7% aqueous hydrochloric acid solution, 105° C. and 20 minutes. After the filtration and washing isopropyl alcohol was added to the filtration residue washed, and the residue was dispersed with a Gohrin Homogenizer Model 15M manufactured by Nihon Seiki Seisakusho Ltd. The solid content of the resulting dispersion was adjusted to 10%, fo llowed by spray drying. Coarse particles were removed by the use of a screen with opening of 250 μm to obtain cellulose powder N (loss in weight on drying: 3.5%, corresponding to Example 2 in JP-A-2-84401). Table 1 shows physical properties of cellulose powder N obtained and physical properties of a cylindrical molded product obtained by compressing cellulose powder N.

Table 2 shows physical properties of a cylindrical molded product obtained by compressing a mixture of equal amounts of cellulose powder N and lactose.

Comparative Example 8

Using Air Jet Sieve, coarse particles were removed from cellulose powder H of Comparative Example 1 with a 75-μm screen and fine particles were removed therefrom with a 38-μm screen to obtain cellulose powder O (loss in weight on drying: 4.0%, corresponding to Example in JP-A-11-152233). Table 1 shows physical properties of cellulose powder O obtained and physical properties of a cylindrical molded product obtained by compressing cellulose powder O.

Table 2 shows physical properties of a cylindrical molded product obtained by compressing a mixture of equal amounts of cellulose powder O and lactose.

Comparative Example 9

The same cellulose dispersion as obtained in Example 5 was stirred (rate of stirring: 4,000 rpm) with a TK homomixer and then subjected to spray drying (dispersion feed rate: 6 L/hr, inlet temperature: 180 to 220° C., and outlet temperature: 50 to 70° C.) to obtain cellulose powder P (loss in weight on drying: 3.8%). Table 1 shows physical properties of cellulose powder P obtained and physical properties of a cylindrical molded product obtained by compressing cellulose powder P. Table 2 shows physical properties of a cylindrical molded product obtained by compressing a mixture, of equal amounts of cellulose powder P and lactose.

Comparative Example 10

Commercially available SP pulp (polymerization degree: 790, and level-off polymerization degree: 220) was chopped and then hydrolyzed in a 10% aqueous hydrochloric acid solution at 105° C. for 5 minutes, and the resulting acid-insoluble residue was filtered, washed and then subjected to pH adjustment and concentration adjustment to obtain a cellulose particle dispersion having a solid content of 17%, a pH of 6.4 and an electric conductivity of 120 μS/cm. The dispersion was dried in a drum dryer (Model KDD-1, mfd. by Kusunoki Kikai Seisakusho Co., Ltd.: steam pressure: 0.35 MPa, drum surface temperature: 136° C., number of revolutions of drum: 2 rpm, and temperature of the dispersion in a reservoir: 100° C.) and then ground with a hammer mill, and coarse particles were removed by the use of a screen with opening of 425 μm to obtain cellulose powder Q (loss in weight on drying: 4.5%, corresponding to Comparative Example 8 in JP-A-6-316535). Table 1 shows physical properties of cellulose powder Q obtained and physical properties of a cylindrical molded product obtained by compressing cellulose powder Q. Table 2 shows physical properties of a cylindrical molded product obtained by compressing a mixture of equal amounts of cellulose powder Q and lactose.

Comparative Example 11

Ten grams of chopped commercially available SP pulp (polymerization degree: 1030, and level-off polymerization degree: 220) was impregnated with a 0.25N solution of hydrochloric acid in isopropyl alcohol and then hydrolyzed at 90° C. for 10 minutes while being stirred so that the shear rate of the starting-material layer became 10 s$^{-1}$. Then, the hydrolysis residue was dried on trays at 40° C. for 24 hours to obtain cellulose powder R (loss in weight on drying: 2.5%, corresponding to Example 8 in RU2050362). Table 1 shows physical properties of cellulose powder R obtained and physical properties of a cylindrical molded product obtained by compressing cellulose powder R. Table 2 shows physical properties of a cylindrical molded product obtained by compressing a mixture of equal amounts of cellulose powder R and lactose.

Example 8

In a polyethylene bag, 20 wt % of cellulose powder C of Example 3, 19.5 wt % of lactose (Pharmatose 100M, available from DMV Corp.), 60 wt % of ethenzamide (mfd. by Iwaki Seiyaku Co., Ltd.) and 0.5 wt % of light silicic anhydride (Aerosil 200, mfd. by Nippon Aerasil Co., Ltd.) were thoroughly mixed for 3 minutes, and magnesium stearate (mfd. by Taihei Kagaku Sangyo Co., Ltd.) was added thereto in an amount of 0.5 wt % based on the total weight of the mixed powder, followed by slow mixing for another 30 seconds. Table 3 shows the angle of repose of the resulting mixed powder.

This mixed powder was compressed into tablets each weighing 100 mg with a rotary tabletting machine (CLEAN-PRESS CORRECT 12HUK, mfd. by Kikusui Seisakusho Ltd.) at a turntable rotational speed of 24 rpm and a compressive force of 3,000 N by the use of a 11R punch with a diameter of 0.6 cm. Table 3 shows physical properties of the tablets.

Example 9

Mixed powder and tablets were prepared by the same procedure as in Example 8 except for using cellulose powder E of Example 5. Table 3 shows the angle of repose of the mixed powder and physical properties of the tablets.

Comparative Example 12

Mixed powder and tablets were prepared by the same procedure as in Example 8 except for using cellulose powder H of Comparative Example 1. Table 3 shows the angle of repose of the mixed powder and physical properties of the tablets.

Comparative Example 13

Mixed powder and tablets were prepared by the same procedure as in Example 8 except for using cellulose powder I of Comparative Example 2 in Example 8. Table 3 shows the angle of repose of the mixed powder and physical properties of the tablets.

Example 10

In a polyethylene bag, 60 wt % of acetaminophen (fine powder type, mfd. by Yoshitomi Fine Chemical Co., Ltd.) and 0.5 wt % of light silicic anhydride (Aerosil 200, mfd. by Nippon Aerasil Co., Ltd.) were mixed for 3 minutes to previously improve the fluidity of the drug. Then, 30 wt % of cellulose powder C of Example 3 and 9.5 wt % of corn starch (available from Nippon Starch Chemical Co., Ltd.) were added thereto, followed by thorough mixing for 3 minutes in the polyethylene bag. Magnesium stearate (mfd. by Taihei Kagaku Sangyo Co., Ltd.) was added thereto in an amount of 0.5 wt % based on the total weight of the mixed powder, followed by slow mixing for further 30 seconds. Table 4 shows the angle of repose of the resulting mixed powder.

This mixed powder was compressed into tablets each weighing 100 mg with a rotary tabletting machine (CLEAN-PRESS CORRECT 12HUK, mfd. by Kikusui Seisakusho Ltd.) at a turntable rotational speed of 53 rpm and a compressive force of 5,000 N by the use of a 11R punch with a diameter of 0.6 cm. Table 4 shows physical properties of the tablets. As the disintegration time of the tablets, a value obtained without a disc is shown. As the rate of dissolution of the drug contained in the tablets, a value obtained at a number of revolutions of a paddle of 100 rpm is shown.

Example 11

In a polyethylene bag, 30 wt % of cellulose powder C of Example 3, 9.5 wt % of crospovidone (Colidon CL, mfd. by BASF), 60 wt % of acetaminophen (fine powder type, mfd. by Yoshitomi Fine Chemical Co., Ltd.) and 0.5 wt % of light silicic anhydride (Aerosil 200, mfd. by Nippon Aerosil Co., Ltd.) were mixed all at once for 3 minutes. Magnesium stearate (mfd. by Taihei Kagaku Sangyo Co., Ltd.) was added thereto in an amount of 0.5 wt % based on the total weight of the mixed powder, follow ed by slow mixing for further 30 seconds. Table 5 shows the angle of repose of the resulting mixed powder.

This mixed powder was compressed into tablets each weighing 100 mg with a rotary tabletting machine (CLEAN-PRESS CORRECT 12HUK, mfd. by Kikusui Seisakusho Ltd.) at a turntable rotational speed of 53 rpm and a compressive force of 5,000 N by the use of a 11R punch with a diameter of 0.6 cm. Table 4 shows physical properties of the tablets. As the disintegration time of the tablets, a value obtained without a disc is shown.

Example 12

In a polyethylene bag, 60 wt % of acetaminophen (fine powder type, mfd. by Yoshitomi Fine Chemical Co., Ltd.) and 0.5 wt % of light silicic anhydride (Aerosil 200, mfd. by Nippon Aerosil Co., Ltd.) were mixed for 3 minutes to previously imp rove the fluidity of the drug. Then, 30 wt % of cellulose powder C of Example 3 and 9.5 wt % of crospovidone (Colidon C L, mfd. by BASF) were added thereto, followed by thorough mixing for 3 minutes in the polyethylene bag. Magnesium stearate (mfd. by Taihei Kagaku Sangyo Co., Ltd.) was added thereto in an amount of 0.5 wt % based on the total weight of the mixed powder, followed by slow mixing for further 30 seconds. Table 5 shows the angle of repose of the resulting mixed powder.

This mixed powder was compressed into tablets each weighing 100 mg with a rotary tabletting machine (CLEAN-PRESS CORRECT 12HUK, mfd. by Kikusui Seisakusho Ltd.) at a turntable rotational speed of 53 rpm and a compressive force of 5,000 N by the use of a 11R punch with a diameter of 0.6 cm. Table 4 shows physical properties of the tablets. As the disintegration time of the tablets, a value obtained without a disc is shown.

Example 13

The process of Example 12 was repeated except for using cellulose powder E of Example 5. Table 5 shows the angle of repose of the resulting mixed powder and physical properties of tablets made of the mixed powder.

Example 14

In a polyethylene bag, 70 wt % of acetaminophen (fine powder type, mfd. by Yoshitomi Fine Chemical Co., Ltd.) and 0.5 wet of light silicic anhydride (Aerosil 200, mfd. by Nippon Aerosil Co., Ltd.) were mixed for 3 minutes to previously improve the fluidity of the drug. Then, 25 wt % of cellulose powder C of Example 3 and 4.5 wt % of sodium croscarmellose (Ac-Di-Sol, mfd. by FMC Corp., sold by Asahi Kasei Co.) were added thereto, followed by thorough mixing for 3 minutes in the polyethylene bag. Magnesium stearate (mfd. by Taihei Kagaku Sangyo Co., Ltd.) was added thereto in an amount of 0.5 wt % based on the total weight of the mixed powder, followed by slow mixing for further 30 seconds. Table 6 shows the angle of repose of the resulting mixed powder.

This mixed powder was compressed into tablets each weighing 180 mg with a rotary tabletting machine (CLEAN-PRESS CORRECT 12HUK, mfd. by Kikusui Seisakusho Ltd.) at a turntable rotational speed of 53 rpm and a compressive force of 10,000 N by the use of a 12R punch with a diameter of 0.8 cm. Table 6 shows physical properties of the tablets. As the disintegration time of the tablets, a value obtained without a disc is shown.

Example 15

The process of Example 14 was repeated except for using cellulose powder E of Example 5. Table 6 shows the angle of repose of the resulting mixed powder and physical properties of tablets made of the mixed powder. As the disintegration time of the tablets, a value obtained without a disc is shown.

Comparative Example 14

The process of Example 10 was repeated except for using cellulose powder H of Comparative Example 1. Table 4 shows the angle of repose of the resulting mixed powder and physical properties of tablets made of the mixed powder. As the disintegration time of the tablets, a value obtained without a disc is shown. As the rate of dissolution of the drug contained in the tablets, a value obtained at a number of revolutions of a paddle of 100 rpm is shown.

Comparative Example 15

The process of Example 10 was repeated except for using cellulose powder I of Comparative Example 2. Table 4 shows the angle of repose of the resulting mixed powder and physical properties of tablets made of the mixed powder. As the disintegration time of the tablets, a value obtained without a disc is shown. As the rate of dissolution of the drug contained in the tablets, a value obtained at a number of revolutions of a paddle of 100 rpm is shown.

Comparative Example 16

The process of Example 11 was repeated except for using cellulose powder H of Comparative Example 1. Table 5 shows the angle of repose of the resulting mixed powder and physical properties of tablets made of the mixed powder. As the disintegration time of the tablets, a value obtained without a disc is shown.

Comparative Example 17

The process of Example 11 was repeated except f or using cellulose powder I of Comparative Example 2. Table 5 shows the angle of repose of the resulting mixed powder and physical properties of tablets made of the mixed powder. As the disintegration time of the tablets, a value obtained without a disc is shown.

Comparative Example 18

The process of Example 12 was repeated except for using cellulose powder H of Comparative Example 1. Table 5 shows the angle of repose of the resulting mixed powder and physical properties of tablets made of the mixed powder. As the disintegration time of the tablets, a value obtained without a disc is shown.

Comparative Example 19

The process of Example 12 was repeated except for using cellulose powder I of Comparative Example 2. Table 5 shows the angle of repose of the resulting mixed powder and physical properties of tablets made of the mixed powder. As the disintegration time of the tablets, a value obtained without a disc is shown.

Comparative Example 20

The process of Example 14 was repeated except for using cellulose powder H of Comparative Example 1. Table 6 shows the angle of repose of the resulting mixed powder and physical properties of tablets made of the mixed powder. As the disintegration time of the tablets, a value obtained without a disc is shown.

Comparative Example 21

The process of Example 14 was repeated except for using cellulose powder I of Comparative Example 2. Table 6 shows the angle of repose of the resulting mixed powder and physical properties of tablets made of the mixed powder. As the disintegration time of the tablets, a value obtained without a disc is shown.

Example 16

Preparation of Nucleus Particles

Into a rolling fluidized-bed coating apparatus ("Multiplex" Model MP-01, mfd. by Powrex; using a Wurster column with side air) was charged 0.7 kg of trimebutin maleate (available from Sumitomo Fine Chem. Co., Ltd.), and sprayed with a 5 wt % hydroxypropylmethyl cellulose (TC-5E, available from Shin-etsu Chemical Co., Ltd.) binder solution (spray air pressure: 0.13 MPa, spray air flow rate: 35 L/min, side air pressure: 0.10 MPa, charged air temperature: 75° C., exhaust temperature: 37° C., air flow rate: 40 m$^3$/hr, and binder solution feed rate: 7 g/min) until its proportion becomes 3 wt % (in terms of solids) based on the weight of trimebutin maleate, followed by pre-granulation. Coarse particles were removed from the pre-granulation product by the use of a screen having opening of 250 µm, and 0.7 kg of the residue was charged into the aforesaid coating apparatus and sprayed with a film coating liquid consisting of 38.1 wt % of an aqueous ethyl cellulose dispersion ("Aquacoat" ECD-30, mfd. by FMC Corp., sold by Asahi Chemical Industry Co.; solid content 30 wt %), 2.9 wt % of triacetin, 38.1 wt % of a 15 wt % aqueous mannitol solution and 20.9 wt % of water (spray air pressure: 0.10 MPa, spray air flow rate: 30 L/min, side air pressure: 0.02 MPA, charged air temperature: 70° C., exhaust temperature: 36° C., air flow rate: 40 m$^3$/hr, and binder solution feed rate: 8 g/min) until its proportion becomes 30 wt % (in terms of solids) based on the weight of the trimebutin maleate pre-granulation product to obtain coated granules. The coated granules were dried on trays at 40° C. for 30 minutes and then subjected to curing (film formation by heating) treatment by drying on trays at 80° C. for 60 minutes to obtain nucleus particles A. Table 7 shows the rate of dissolution of trimebutin maleate in nucleus particles A after 1 minute.

(Preparation of Nucleus Particle-Containing Tablets)

In a die (manufactured by Kikusui Seisakusho Ltd. from material SUK 2,3) was placed 0.2 g of a sample consisting of 59 wt % of cellulose powder B of Example 2, 26 wt % of nucleus particles A and 15 wt % of sodium croscarmellose (Ac-Di-Sol, mfd. by FMC Corp., sold by Asahi Kasei Co.), and compressed with a flat punch having a diameter of 0.8 cm (manufactured by Kikusui Seisakusho Ltd. from material SUK 2,3). The compression stress was maintained at 1,400 N for 10 seconds to obtain nucleus particle-containing tablets A. As a compressing machine, PCM-1A manufactured by Aikoh Engineering Co., Ltd. was used. Table 7 shows the tablet hardness of nucleus particle-containing tablets A and the rate of dissolution of trimebutin maleate in nucleus particle-containing tablets A after 1 minute.

Example 17

Nucleus particle-containing tablets B were obtained by the same procedure as in Example 16 except for changing their composition and the compression stress as follows; cellulose powder B of Example 2: 59 wt %, nucleus particles A: 26 wt %, corn starch: 10 wt %, sodium croscarmellose: 5 wt %, and compression stress: 1,500 N. Table 7 shows the tablet hardness of nucleus particle-containing tablets A and the rate of dissolution of trimebutin maleate in nucleus particle-containing tablets B after 1 minute.

Example 18

Nucleus particle-containing tablets C were obtained by the same procedure as in Example 16 except for changing their composition as follows; cellulose powder B of Example 2: 59 wt %, nucleus particles A: 26 wt %, partly pregelatinized starch ("PCS" PC-10, available from Asahi Kasei Co.): 10 wt %, and sodium croscarmellose: 5 wt %. Table 7 shows the tablet hardness of nucleus particle-containing tablets C and the rate of dissolution of trimebutin maleate in nucleus particle-containing tablets C after 1 minute.

Example 19

Preparation of Nucleus Particles

A spherical nucleus ("Celfia" CP-305, available from Asahi Kasei Co.) was charged into a rolling fluidized-bed coating apparatus ("Multiplex" Model MP-25, mfd. by Powrex) and sprayed with a drug-coating solution consisting of 10 parts of riboflavin, 2 wt % of hydroxypropyl cellulose (L type, available from Nippon Soda Co., Ltd.) and 88 wt % of water, to obtain layering granules containing 2 wt % of riboflavin. Into a rolling fluidized-bed coating apparatus ("Multiplex" Model MP-01, mfd. by Powrex) was charged 1.5 kg of the layering granules, and sprayed with a film coating liquid consisting of 32.0 wt % of an aqueous ethyl cellulose dispersion ("Aquacoat" ECD-30, mfd. by FMC Corp., sold by Asahi Kasei Co.; solid content 30 wt %), 2.4 wt % of triethyl citrate, 30 wt % of a 10 wt % aqueous hydroxypropylmethyl cellulose solution and 35.6 wt % of water (spray air pressure: 0.16 MPa, spray air flow rate: 40 L/min, charged air temperature: 75° C., exhaust temperature: 36° C., air flow rate: 75 m$^3$/hr, and binder solution feed rate: 21 g/min) until its proportion becomes 50 wt % (in terms of solids) based on the weight of the layering granules to obtain coated granules. The coated granules were dried on trays at 50° C. for 30 minutes and then subjected to curing (film formation by heating) at 80° C. for 60 minutes to obtain nucleus particles B. Table 8 shows the rate of dissolution of riboflavin in nucleus particles B after 30 minutes.

(Preparation of Nucleus Particle-Containing Tablets)

Nucleus particle-containing tablets D were obtained by the same procedure as in Example 16 except for changing their composition and the compression stress as follows; cellulose powder B of Example 2: 50 parts, nucleus particles B: 45 parts, sodium croscarmellose: 5 parts, and compression stress: 2,200 N. Table 8 shows the tablet hardness of nucleus particle-containing tablets D and the rate of dissolution of riboflavin in nucleus particle-containing tablets D after 30 minutes.

Comparative Example 22

Nucleus particle-containing tablets E were obtained by the same procedure as in Example 16 except for Using cellulose powder H of Comparative Example 1. Table 7 shows the tablet hardness of nucleus particle-containing tablets E. Nucleus particle-containing tablets E were hardly disintegrated in a dissolution test, so that the rate of dissolution of trimebutin maleate in nucleus particle-containing tablets E could not be measured.

Comparative Example 23

Nucleus particle-containing tablets F were obtained by the same procedure as in Example 16 except for using cellulose powder I of Comparative Example 2 and changing the compression stress to 1,700 N. Table 7 shows the tablet hardness of nucleus particle-containing tablets F and the rate of dissolution of trimebutin maleate in nucleus particle-containing tablets F after 1 minute.

Comparative Example 24

Nucleus particle-containing tablets G were obtained by the same procedure as in Example 17 except for using cellulose powder I of Comparative Example 2 and changing the compression stress to 2,000 N. Table 7 shows the tablet hardness of nucleus particle-containing tablets G and the rate of dissolution of trimebutin maleate in nucleus particle-containing tablets G after 1 minute.

Comparative Example 25

Nucleus particle-containing tablets H were obtained by the same procedure as in Example 18 except for using cellulose powder I of Comparative Example 2 and changing the compression stress to 1,800 N. Table 7 shows the tablet hardness of nucleus particle-containing tablets H and the rate of dissolution of trimebutin maleate in nucleus particle-containing tablets H after 1 minute.

Comparative Example 26

Nucleus particle-containing tablets I were obtained by the same procedure as in Example 19 except for using cellulose powder I of Comparative Example 2 and changing the compression stress to 3,300 N. Table 8 shows the tablet hardness of nucleus particle-containing tablets I and the rate of dissolution of riboflavin in nucleus particle-containing tablets I after 30 minutes.

TABLE 3

| | | | | | Powder physical properties | | | | | | | |
|---|---|---|---|---|---|---|---|---|---|---|---|---|
| | | | | LD of particles before drying | Particles capable of remaining on a 250-μm screen [%] | LD of particles of 75 μm or less | Apparent specific volume [cm$^3$/g] | Apparent tapping specific volume [cm$^3$/g] | Average particle size [μm] | Angle of repose [°] | Specific surface area [m$^2$/g] | |
| | | Cellulose powder | Polymerization degree | | | | | | | | Water vapor | Nitrogen |
| Example | 1 | A | 220 | 3.1 | 0 | 2.1 | 4.1 | 2.6 | 48 | 46 | 93 | 1.1 |
| | 2 | B | 270 | 3.4 | 0 | 2.5 | 4.7 | 2.7 | 45 | 48 | 91 | 1.2 |
| | 3 | C | 270 | 4.0 | 1 | 3.0 | 5.1 | 2.8 | 50 | 50 | 90 | 1.4 |
| | 4 | D | 270 | 3.4 | 4 | 2.5 | 4.4 | 2.6 | 105 | 44 | 92 | 1.0 |
| | 5 | E | 330 | 4.6 | 3 | 3.5 | 5.3 | 2.9 | 45 | 51 | 90 | 1.5 |
| | 6 | F | 375 | 5.0 | 2 | 4.0 | 5.8 | 3.2 | 49 | 51 | 89 | 1.6 |
| | 7 | G | 440 | 5.3 | 3 | 4.3 | 6.3 | 3.3 | 38 | 54 | 88 | 1.7 |
| Comparative Example | 1 | H | 220 | 2.9 | 6 | 2.3 | 5.4 | 2.7 | 47 | 56 | 84 | 1.9 |
| | 2 | I | 220 | 2.9 | 0 | 1.8 | 3.1 | 2.3 | 49 | 44 | 93 | 1.0 |
| | 3 | J | 488 | 5.6 | 3 | 4.7 | 7.1 | 2.5 | 50 | 65 | 84 | 0.9 |
| | 4 | K | 145 | 2.5 | 0 | 1.6 | 2.0 | 1.6 | 40 | 35 | 86 | 0.6 |
| | 5 | L | 220 | 2.9 | 0 | 1.6 | 5.0 | 2.3 | 12 | 57 | 83 | 2.3 |
| | 6 | M | 330 | 5.0 | 0 | 1.7 | 2.0 | 1.5 | 19 | 63 | 94 | 0.6 |
| | 7 | N | 220 | 2.4 | 0 | 1.5 | 5.7 | 2.8 | 48 | 55 | 82 | 24.1 |
| | 8 | O | 220 | 2.9 | 0 | 2.5 | 6.3 | 2.8 | 50 | 59 | 84 | 2.4 |
| | 9 | P | 330 | 2.7 | 0 | 1.6 | 2.9 | 2.2 | 30 | 43 | 92 | 1.2 |
| | 10 | Q | 380 | 5.6 | 15 | 4.6 | 5.5 | 3.2 | 82 | 55 | 84 | 0.8 |
| | 11 | R | 356 | 2.0 | 8 | 1.9 | 3.6 | 2.3 | 75 | 46 | 91 | 1.5 |

TABLE 3-continued

|  |  | Physical properties of a cylindrical molded product of 100% cellulose powder | | | |
|---|---|---|---|---|---|
|  |  | Yield pressure [MPa] | Ka [l/min] | Hardness [N] | Disintegration time [sec] |
| Example | 1 | 29 | 0.0270 | 185 | 15 |
|  | 2 | 27 | 0.0240 | 201 | 55 |
|  | 3 | 23 | 0.0230 | 252 | 70 |
|  | 4 | 29 | 0.0250 | 190 | 35 |
|  | 5 | 21 | 0.0226 | 310 | 75 |
|  | 6 | 24 | 0.0222 | 248 | 85 |
|  | 7 | 27 | 0.0215 | 203 | 108 |
| Comparative Example | 1 | 26 | 0.0195 | 191 | 150 |
|  | 2 | 40 | 0.0306 | 161 | 12 |
|  | 3 | 32 | 0.0170 | 188 | 290 |
|  | 4 | 45 | 0.0350 | 130 | 7 |
|  | 5 | 33 | 0.0175 | 177 | 214 |
|  | 6 | 43 | 0.0405 | 100 | 5 |
|  | 7 | 36 | 0.0185 | 190 | 250 |
|  | 8 | 24 | 0.0188 | 210 | 220 |
|  | 9 | 44 | 0.0266 | 150 | 19 |
|  | 10 | 35 | 0.0177 | 174 | 218 |
|  | 11 | 39 | 0.0273 | 166 | 15 |

TABLE 2

|  |  |  | Physical properties of a molded product of a mixture of equal amounts of cellulose powder and lactose | |
|---|---|---|---|---|
|  |  | Cellulose powder | Hardness [N] | Disintegration time [sec] |
| Example | 1 | A | 154 | 12 |
|  | 2 | B | 171 | 35 |
|  | 3 | C | 220 | 52 |
|  | 4 | D | 161 | 15 |
|  | 5 | E | 281 | 54 |
|  | 6 | F | 217 | 65 |
|  | 7 | G | 172 | 72 |
| Comparative Example | 1 | H | 164 | 130 |
|  | 2 | I | 131 | 9 |
|  | 3 | J | 158 | 250 |
|  | 4 | K | 100 | 6 |
|  | 5 | L | 144 | 195 |
|  | 6 | M | 70 | 4 |
|  | 7 | N | 162 | 215 |
|  | 8 | O | 179 | 190 |
|  | 9 | P | 118 | 15 |
|  | 10 | Q | 143 | 202 |
|  | 11 | R | 132 | 12 |

TABLE 3

|  |  | Powder physical property | Tablet properties | | |
|---|---|---|---|---|---|
|  |  | Angle of repose [°] | Hardness [N] | CV value [%] | Disintegration time [sec] |
| Example | 8 | 49 | 48 | 0.6 | 10 |
|  | 9 | 45 | 59 | 0.7 | 15 |
| Comparative Example | 10 | 52 | 42 | 1.9 | 25 |
|  | 11 | 42 | 32 | 0.5 | 9 |

TABLE 4

|  |  | Tablet physical properties | | | | |
|---|---|---|---|---|---|---|
|  |  | Powder physical property | | | | Rate of dissolution after 5 minutes [%] |
|  |  | Angle of repose [°] | Hardness [N] | CV value [%] | Disintegration time [sec] | |
| Example | 10 | 51 | 62 | 0.8 | 15 | 86.7 |
| Comparative Example | 14 | 58 | 51 | 1.2 | 30 | 77.4 |
|  | 15 | 46 | 34 | 0.9 | 10 | 99.7 |

TABLE 5

|  |  | Powder physical property | Tablet properties | | |
|---|---|---|---|---|---|
|  |  | Angle of repose [°] | Hardness [N] | CV value [%] | Disintegration time [sec] |
| Example | 11 | 50 | 66 | 0.9 | 10 |
|  | 12 | 49 | 74 | 0.6 | 11 |
|  | 13 | 50 | 81 | 0.8 | 11 |
| Comparative Example | 16 | 57 | 55 | 1.5 | 12 |
|  | 17 | 46 | 39 | 0.9 | 10 |
|  | 18 | 56 | 61 | 1.1 | 11 |
|  | 19 | 45 | 40 | 0.8 | 11 |

TABLE 6

| | Powder physical property Angle of repose [°] | Tablet physical properties | | | |
|---|---|---|---|---|---|
| | | Hardness [N] | CV value [%] | Disintegration time [sec] | Degree of wear [%] |
| Example 14 | 52 | 79 | 0.5 | 15 | 0.07 |
| 15 | 53 | 91 | 0.7 | 18 | 0.02 |
| Comparative 20 | 59 | 68 | 1.1 | 31 | 0.10 |
| Example 21 | 48 | 59 | 0.5 | 15 | 0.70 |

TABLE 7

| | | Nucleus particle-containing tablet | Hardness [N] | Rate of dissolution after 1 minute [%] |
|---|---|---|---|---|
| Nucleus particle A | | — | — | 12.0 |
| Example | 16 | A | 44 | 19.8 |
| | 17 | B | 41 | 19.0 |
| | 18 | C | 40 | 21.0 |
| Comparative | 22 | E | 44 | — |
| Example | 23 | F | 43 | 27.2 |
| | 24 | G | 46 | 25.5 |
| | 25 | H | 45 | 33.9 |

TABLE 8

| | | Nucleus particle-containing tablet | Hardness [N] | Rate of dissolution after 1 minute [%] |
|---|---|---|---|---|
| Nucleus particle B | | — | — | 7.5 |
| Example | 19 | D | 44 | 9.8 |
| Comparative Example | 26 | I | 44 | 17.0 |

Industrial Applicability

Since the cellulose powder of the present invention is excellent in fluidity and disintegrating property while retaining a good compression moldability, the cellulose powder makes it possible to provide tablets having high hardness without retardation of their disintegration, especially, even when the tablets are molded under a high striking pressure. Furthermore, the cellulose powder makes it possible to provide tablets which maintain their uniformity in weight even when their drug content is high and have a good balance between hardness and disintegrating property. Therefore, the cellulose powder of the present invention is very useful for miniaturizing, for example, tablets containing an active ingredient having a large specific volume, or tablets having a high content of an active ingredient. Moreover, in granule-containing tablets containing a coated active ingredient, the cellulose powder of the present invention exhibits such an advantage that the compression molding of the tablets hardly destroys the granules, hardly damages the coating films of the granules and hardly cause a change in drug-releasing properties.

The invention claimed is:

1. A cellulose powder having an average polymerization degree of 150-450, an average L/D value of particles of 2.0-4.5 for 75 μm or less, an average particle size of 20-105 μm, an apparent specific volume of 4.0-7.0 cm$^3$/g, an apparent tapping specific volume of 2.4-4.5 cm$^3$/g, an angle of repose of 52° or less, and a specific surface area of 85 m$^2$/g or more as measured by water vapor adsorption, wherein the average polymerization degree of said powder is 5 to 300 higher than the level-off polymerization degree for said cellulose powder, said level-off polymerization degree being measured by a viscosity method after hydrolysis of the cellulose powder in boiling 2.5N hydrochloric acid for 15 minutes, wherein the breaking load of tablets obtained by compressing 0.5 g of the cellulose powder at 20 MPa is 190 N or more and the disintegration time of the tablets is 130 seconds or less.

2. The cellulose powder according to claim 1, wherein the average polymerization degree is 230-450.

3. The cellulose powder according to claim 1 or 2, wherein the breaking load of tablets is 150 N or more and the disintegration time of the tablets is 120 seconds or less wherein the tablets are obtained by compressing 0.5 g of a mixture of equal amounts of the cellulose powder and lactose at 80 MPa.

4. An excipient comprising the cellulose powder according to claim 1 or 2.

5. A molded product comprising the cellulose powder according to claim 1 or 2.

6. The molded product according to claim 5, wherein the molded product is tablets containing one or more active ingredients.

7. The molded product according to claim 6, wherein the molded product contains the active ingredient(s) in a proportion of 30 wt % or more.

8. The molded product according to claim 5, wherein the molded product is coated.

9. The molded product according to claim 5, wherein the molded product is rapidly disintegrable.

10. The molded product according to claim 5, wherein the molded product contains a fluidizing agent.

11. The cellulose powder according to claim 1, which is produced by a process comprising hydrolyzing a natural cellulosic material under conditions of acid concentration and/or temperature which are milder than conditions for reaching the level-off polymerization degree that is inherent to natural cellulosic material.

12. The cellulose powder according to claim 1, wherein the average polymerization degree of said powder is about 10 to about 250 higher than the level-off polymerization degree.

13. The cellulose powder according to claim 1, wherein the average polymerization degree of said powder is 50 to about 250 higher than the level-off polymerization degree.

14. The cellulose powder according to claim 1, wherein the average polymerization degree of said powder is 110 to about 250 higher than the level-off polymerization degree.

15. The cellulose powder according to claim 1, wherein the average polymerization degree of said powder is 155 to about 250 higher than the level-off polymerization degree.

* * * * *